(12) United States Patent
Ranjan et al.

(10) Patent No.: US 9,920,014 B2
(45) Date of Patent: Mar. 20, 2018

(54) SELECTIVE INHIBITION OF BACTERIAL TOPOISOMERASE I

(71) Applicants: THE FLORIDA INTERNATIONAL BOARD OF TRUSTEES MODESTO A. MAIDIQUE CAMPUS, Miami, FL (US); CLEMSON UNIVERSITY, Clemson, SC (US)

(72) Inventors: Nihar Ranjan, Clemson, SC (US); Dev P. Arya, Greenville, SC (US); Fenfei Leng, Palmetto Bay, FL (US)

(73) Assignees: THE FLORIDA INTERNATIONAL UNIVERSITY BOARD OF TRUSTEES, Miami, FL (US); CLEMSON UNIVERSITY, Clemson, SC (US)

( * ) Notice: Subject to any disclaimer, the term of this patent is extended or adjusted under 35 U.S.C. 154(b) by 0 days.

(21) Appl. No.: 15/022,868

(22) PCT Filed: Sep. 19, 2014

(86) PCT No.: PCT/US2014/056619
§ 371 (c)(1),
(2) Date: Mar. 17, 2016

(87) PCT Pub. No.: WO2015/042438
PCT Pub. Date: Mar. 26, 2015

(65) Prior Publication Data
US 2016/0229810 A1    Aug. 11, 2016

Related U.S. Application Data

(60) Provisional application No. 61/879,968, filed on Sep. 19, 2013.

(51) Int. Cl.
| | | |
|---|---|---|
| C07D 235/20 | (2006.01) | |
| A61K 31/496 | (2006.01) | |
| A61K 31/497 | (2006.01) | |
| A61K 45/06 | (2006.01) | |

(52) U.S. Cl.
CPC .......... *C07D 235/20* (2013.01); *A61K 31/496* (2013.01); *A61K 31/497* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 4,463,173 A * | 7/1984 | Jung | ............... | C07C 205/35 540/215 |
| 5,719,139 A * | 2/1998 | Lohmann | ............... | C07F 9/5683 514/210.04 |
| 5,770,617 A | 6/1998 | LaVoie et al. | | |
| 5,968,933 A | 10/1999 | Denny et al. | | |
| 2011/0046982 A1* | 2/2011 | Arya | ............... | A61K 31/7034 705/3 |

OTHER PUBLICATIONS

Ranjan et al. Med. Chem. Commun., 2014, 5, 816-825.*
Bansal, Sandhya et al., "Old class but new dimethoxy analogue of benzimidazole: a bacterial topoisomerase I inhibitor," *International Journal of Antimicrobial Agents*, 2010, 35:186-190.

* cited by examiner

*Primary Examiner* — Emily Bernhardt
(74) *Attorney, Agent, or Firm* — Saliwanchik, Lloyd & Eisenschenk

(57) ABSTRACT

The present invention provides novel bisbenzimidazole compounds and methods of using the compounds as antibacterial agents.

13 Claims, 12 Drawing Sheets

Hoechst 33258 based bisbenzimidazole derivatives
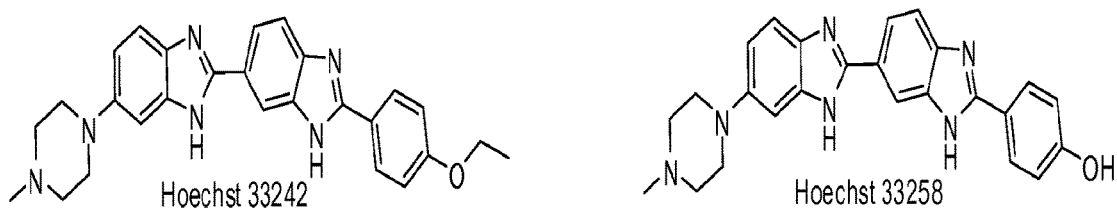
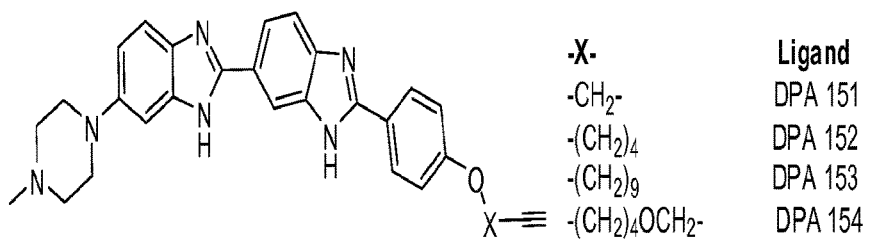
| -X- | Ligand |
|---|---|
| -CH$_2$- | DPA 151 |
| -(CH$_2$)$_4$- | DPA 152 |
| -(CH$_2$)$_9$- | DPA 153 |
| -(CH$_2$)$_4$OCH$_2$- | DPA 154 |
FIGURE 1

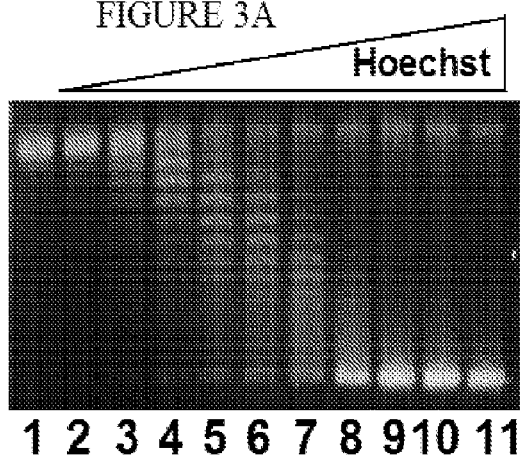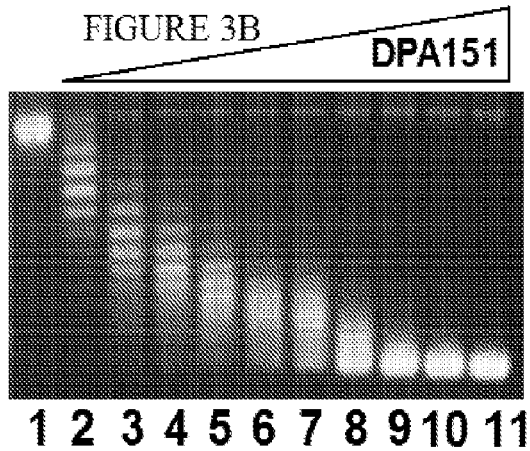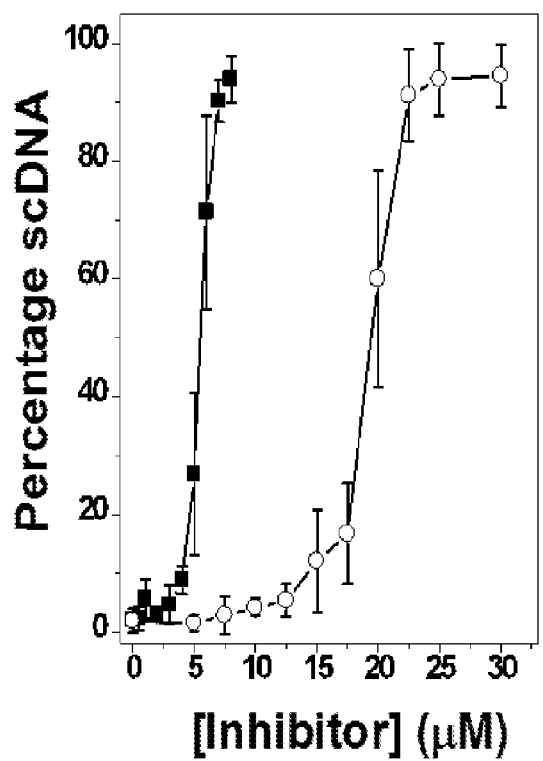

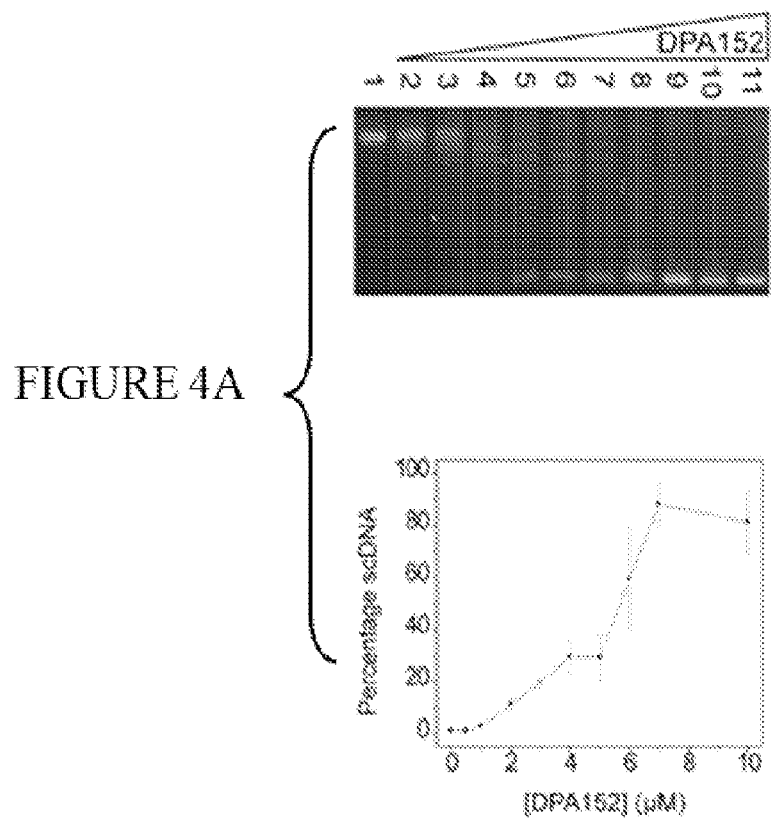
FIGURE 4A
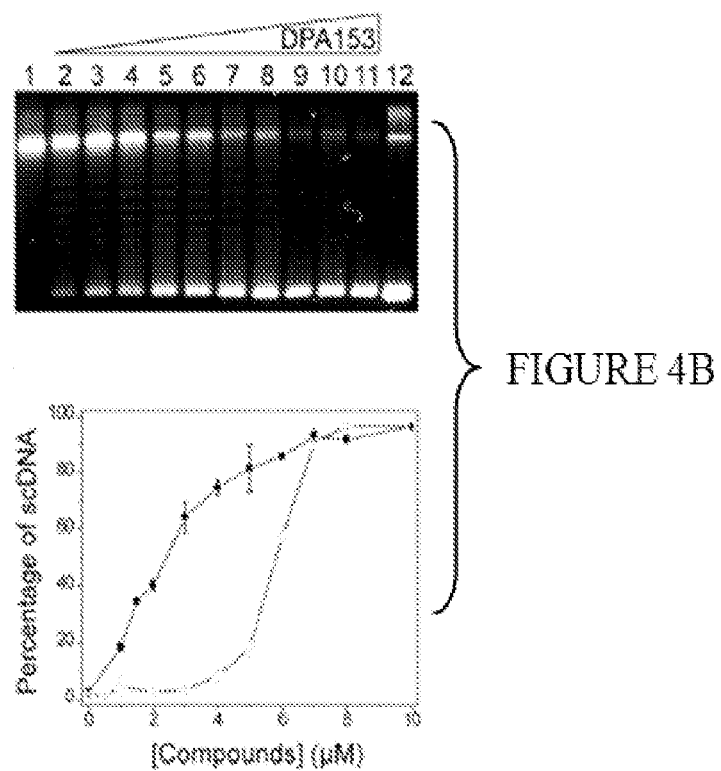
FIGURE 4B
FIGURES 4A-4B

SELECTIVE INHIBITION OF BACTERIAL TOPOISOMERASE I

CROSS-REFERENCE TO A RELATED APPLICATION

This application is a National Stage Application of International Application No. PCT/US2014/056619, filed Sep. 19, 2014; which claims the benefit of U.S. Provisional Application Ser. No. 61/879,968, filed Sep. 19, 2013, the disclosures of which are incorporated herein by reference in their entirety.

GOVERNMENT SUPPORT

This invention was made with government support under CA125724 awarded by the National Institutes of Health. The government has certain rights in the invention.

BACKGROUND OF INVENTION

New approaches for the discovery of antibacterial drugs are paramount to our efforts in the continuing fight against bacterial resistance. In this regard, enzyme inhibitors that selectively target a bacterial enzyme over their human counterpart offer unique opportunities for such selective inhibition approaches. Bacterial DNA topoisomerases are one such class of enzymes that help in regulating DNA topology (Tse-Dinh, Y. *Infect. Disord.: Drug Targets* (2007) 7, 3-9; Tse-Dinh, Y. *Nucleic Acids Research* (2009) 37, 731-737). The cellular functions of topoisomerases include relaxing (+) and (−) supercoil in DNA as well as in introducing supercoils to their DNA substrates (Champoux, J. J. *Annu. Rev. Biochem.* (2001), 70, 369-413). These functions of DNA topoisomerases can be used to develop anticancer or antibacterial agents (Tse-Dinh, Y. *Nucleic Acids Research* (2009) 37, 731-737; Pommier, Y. *Chem. Rev.* (2009) 109, 2894-2902). The therapeutic interest in the development of small molecules as inhibitors of DNA topoisomerase lies in their ability to act as both cleavable complex stabilizing agents as well as in their ability to bind at the ATP binding site (Tse-Dinh, Y. *Nucleic Acids Research* (2009) 37, 731-737).

A number of small molecules have been discovered that poison the functions of DNA topoisomerases. These include camptothecin and its derivatives, intercalators and compounds that interact with the minor groove of B-DNA such as bisbenzimidazoles (Hsiang Y. H. et al., *Journal of Biological Chemistry* (1985) 260, 14873-14878; Bailly, C., Targeting DNA and topoisomerase I with indolocarbazole antitumor agents. In *Small Molecule DNA and RNA Binders* (2003) Vol. 2; 2, pp 538-575; Bailly, C., *Curr. Med. Chem.* (2000) 7, 39-58; Hande, K. R., *Eur. J. Cancer* (1998) 34, 1514-1521; Xu, Z. et al., *Biochemistry* (1998) 37, 3558-3566; Froelich-Ammon, S. J. and Osheroff, N., *J. Biol. Chem.* (1995) 270, 21429-32; Chen, A. Y. et al., *Proceedings of the National Academy of Sciences* (1993) 90, 8131-8135; Chen, A. Y. et al., *Cancer Research* (1993) 53, 1332-1337). Benzimidazoles are an important class of compounds that display a widespread range of biological activities. Halogenated monobenzimidazoles have shown antimycobacterial activity better than isoniazid (Kazimierczuk, Z. et al., *Eur. J. Med. Chem.* (2005) 40, 203-208). Similarly, triazolyl derivatized monobenzimidazoles have displayed antimicrobial properties (Jadhav, G. R. et al., *Eur. J. Med. Chem.* (2009) 44, 2930-2935). In comparison to abundant literature reports on the biological properties of monobenzimidazoles, studies on the antimicrobial properties of bisbenzimidazoles (particularly those modeled from Hoechst 33258) are very limited (Chen, A. Y. et al., *Cancer Research* (1993) 53, 1332-1337; Bansal, S. et al., *Int. J. Antimicrob. Agents* (2010) 35, 186-190). Hoechst 33258 is a bisbenzimidazole compound that has been a subject of intense study for over three decades due to its binding to AT rich duplex DNA structures (Willis, B. and Arya, D. P., *Biochemistry* (2010) 49, 452-469; Willis, B. and Arya, D. P., *Biochemistry* (2006) 45, 10217-10232; Correa, B. J. et al., *Bioorg. Med. Chem. Lett.* (2006) 16, 3745-3750).

BRIEF SUMMARY

The present invention provides novel bisbenzimidazole compounds and methods of using the compounds as antibacterial agents.

According to one embodiment of the present invention, Hoechst 33258 based bisbenzimidazoles, containing a terminal hydrophobic group, are effective, and selective, antibacterial agents. In specific embodiments these compounds, have a terminal alkyne, and are effective inhibitors of *E. coli.* topoisomerase I.

These bisbenzimidazoles display topoisomerase I inhibition that is much better than Hoechst 33342 or Hoechst 33258, with $IC_{50}$ values in the range of 2.47-6.63 μM. The bisbenzimidazoles of the subject invention also display selective inhibition of *E. coli.* topoisomerase I over DNA gyrase, human topoisomerases I and II, and effectively inhibit bacterial growth.

In one aspect, the present invention provides compounds of Formula (I):

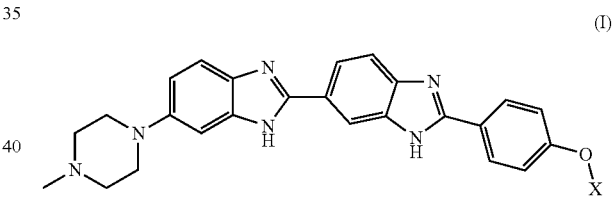

(I)

and salts and derivatives thereof, wherein X is a hydrophobic group.

In a specific embodiment, X comprises a terminal alkyne group attached through a hydrophobic linker to the oxygen.

Derivatives of the compounds described herein include any pharmaceutically acceptable ester, salt of an ester, alcohol, diol, ether, aldehyde, ketone, carboxylic acid, or enol of a compound that can be made from the compound by a chemical or physical process. Examples of derivatives include, but are not limited to, the monobenzimidazole (instead of the bisbenzimidazole), the molecule with the piperzine removed, and the molecule with substituents on the aromatic rings.

In specific embodiments, the hydrophobic group, or the linker, may comprise alkyl, heteroalkyl, and/or aryl groups. Including, for example, the linkers $CH_2$, $(CH_2)_4$, $(CH_2)_9$, and $(CH_2)_4OCH_2$, which are specifically exemplified herein.

As used herein, alkyl means straight or branched chain, saturated or mono- or polyunsaturated hydrocarbon groups having from 1 to 25 carbon atoms, and $C_{1-X}$ alkyl means straight or branched chain alkyl groups containing from one up to X carbon atoms, and includes alkyls, alkenyl, and alkynyls. For example, $C_{1-6}$ alkyl means straight or branched chain alkyl groups containing from 1 up to 6 carbon atoms.

Cycloalkyl includes a nonaromatic monocyclic or multicyclic ring system, including fused and spiro rings, of from about three to about 10 carbon atoms. A cyclic alkyl may optionally be partially unsaturated.

Heteroalkyl means a straight or branched-chain having from one to 25 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms.

Aryl means an aromatic monocyclic or multicyclic carbocyclic ring system, including fused and spiro rings, containing from about six to about 14 carbon atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide.

The alkyl group may have any number of carbons from 1-25 and can be in any range therebetween, including, for example, 2 to 20, 5 to 15, 5 to 10, and any other range.

Additional aspects of the present invention provide pharmaceutical compositions comprising one or more of the compounds of Formula (I), and one or more pharmaceutically acceptable carriers and/or diluents. In certain embodiments, the pharmaceutical compositions can also include additional pharmaceutically active compounds known in the art.

The present invention further provides methods for treating bacterial infections in subjects in need thereof, comprising administering to the subject one or more of the compounds of Formula (I).

The present invention also provides methods of inhibiting topoisomerase I in bacteria, comprising administering, to one or more bacteria, one or more of the compounds of Formula (I).

Embodiments of the present invention can also be provided in the form of kits.

The methods, compositions and kits described herein can be used in connection with pharmaceutical, medical, veterinary, and disinfection applications, as well as fundamental biological research and methodologies, as would be identifiable by a skilled person upon reading of the present disclosure.

BRIEF DESCRIPTION OF DRAWINGS

FIG. 1 shows Hoechst 33258 functionalized bisbenzimidazoles of the present invention.

FIGS. 3A-3C show the inhibitory activities of Hoechst 33258 and DPA 151 against *E. coli* DNA topoisomerase I. Inhibition assays against *E. coli* DNA topoisomerase I were performed as described in the Materials and Methods section. The plasmid DNA molecules were isolated and subjected to 1% agarose gel electrophoresis in the absence of chloroquine. (A) The inhibition activities of Hoechst 33258 against *E. coli* DNA topoisomerase I. Lanes 1 to 11 contain 0, 5, 7.5, 10, 12.5, 15, 20, 22.5, 25, 25.5, 30 μM of Hoechst 33258, respectively. (B) The inhibition activities of DPA 151 against *E. coli* DNA topoisomerase I. Lanes 1 to 11 contain 0, 1.0, 1.5, 2.0, 3.0, 4.0, 5.0, 6.0, 7.0, 8.0, 10 μM of DPA151 respectively. (C) The quantification analyses of the inhibitory activities of Hoechst 33258 (open circles) and DPA 151 (closed squares) against *E. coli* DNA topoisomerase I. The values of IC$_{50}$ (the half maximal inhibitory concentration) were obtained from these analyses. Standard deviation was obtained from three independent determinations. scDNA represents supercoiled DNA.

FIGS. 4A-4B show the inhibitory activities of compounds (a) DPA152 and (b) DPA153 against *E. coli* DNA topoisomerase I. The *E. coli* DNA topoisomerase I inhibition assays were performed as described in the Materials and Methods. The plasmid DNA molecules were isolated and subjected to 1% agarose gel electrophoresis in the absence of chloroquine. (a) Lanes 1 to 11 contain 0, 0.5, 1.0, 2.0, 3.0, 4.0, 5.0, 6.0, 7.0, 8.0, and 10.0 μM of DPA152, respectively. The bottom panel shows the quantification analysis of the inhibitory activities of DPA152. (b) Lanes 1 to 11 contain 0, 1.0, 1.5, 2.0, 3.0, 4.0, 5.0 6.0, 7.0, 8.0, and 10 μM of DPA153, respectively. Lane 12 is the supercoiled plasmid DNA pBAD-GFPuv. The bottom panel shows the quantification analysis of the inhibitory activities of DPA153.

DETAILED DISCLOSURE

Figure 2:
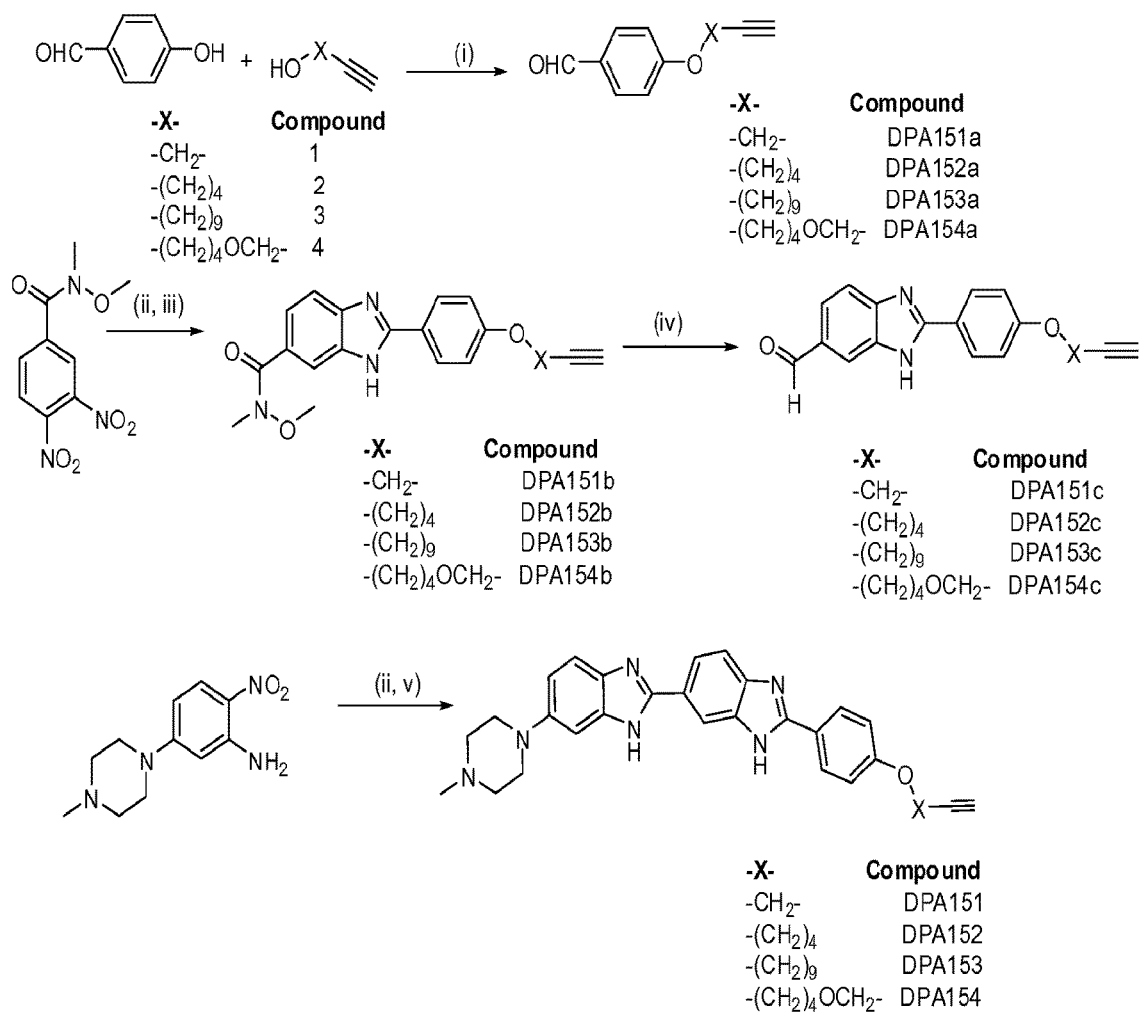
FIG. 2 illustrates the strategy for synthesis of ligands (DPA 151-154) to construct the alkyl linkers described herein. Reagent and conditions (i) PPh$_3$, DIAD, 1,4 dioxane, dichloromethane, rt, overnight, 50-85%, (ii) Pd—C, H$_2$, ethanol, rt, 5 h, gaunt, (iii) DPA 151a-DPA 154a, ethanol, Na$_2$S$_2$O$_5$, H$_2$O, reflux, 12-14 h, 61-85% (for two steps), (iv) THF-ether, LAH, −78° C. to 0° C., 6-12 h, 55-73%, (v) DPA 151c-DPA 154c, ethanol, Na$_2$S$_2$O$_5$, H$_2$O, reflux, overnight, 50-72% (for two steps).
Figure 5:
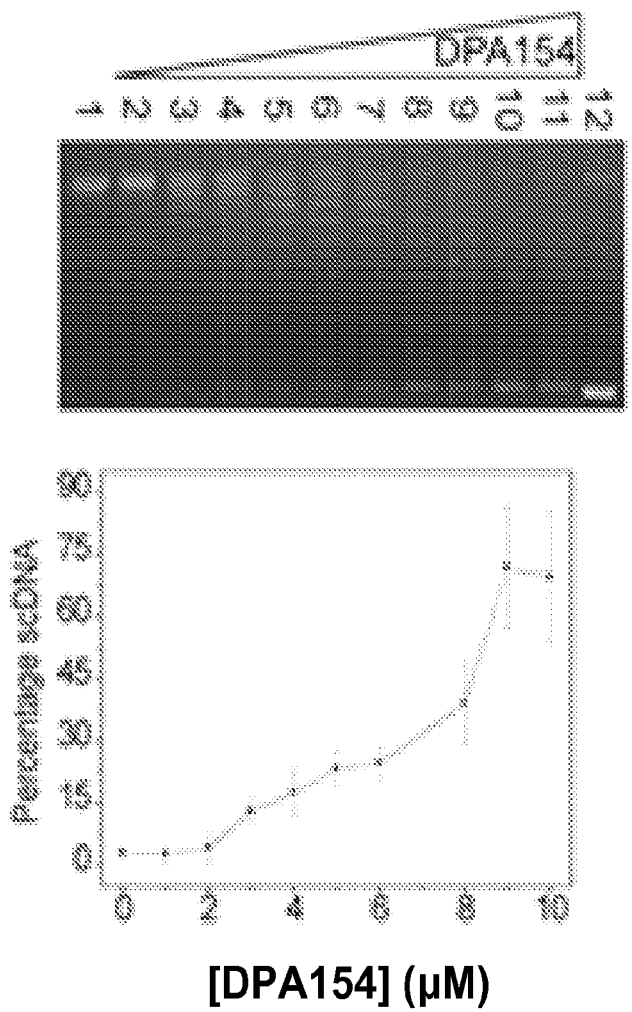
FIG. 5 shows the inhibitory activities of compounds DPA154 against *E. coli* DNA topoisomerase I. The *E. coli* DNA topoisomerase I inhibition assays were performed as described in the Materials and Methods. The plasmid DNA molecules were isolated and subjected to 1% agarose gel electrophoresis in the absence of chloroquine. Lanes 1 to 11 contain 0, 1.0, 2.0, 3.0, 4.0, 5.0, 6.0, 7.0, 8.0, 9.0, and 10.0 μM of DPA154, respectively. Lane 12 is the supercoiled plasmid DNA pBAD-GFPuv. The bottom panel shows the quantification analysis of the inhibitory activities of DPA154.

According to one embodiment of the present invention, Hoechst 33258 based bisbenzimidazoles, containing a terminal hydrophobic group are effective, and selective, antibacterial agents. In specific embodiments these compounds, have a terminal alkyne, and are effective inhibitors of E. coli. topoisomerase I.

These bisbenzimidazoles display topoisomerase I inhibition that is much better than Hoechst 33342 or Hoechst 33258, with $IC_{50}$ values in the range of 2.47-6.63 µM. The bisbenzimidazoles of the subject invention also display selective inhibition of E. coli. topoisomerase I over DNA gyrase, human topoisomerases I and II, and effectively inhibit bacterial growth.

The synthesis, nucleic acid binding, topoisomerase I activity, and antimicrobial activity of Hoechst 33258 functionalized bisbenzimidazoles is described herein. Examples of the compounds of the present invention are shown in FIG. 1.

In accordance with specific embodiments of the present invention it has been found that the addition of an alkyne functionalized alkyl chain converts Hoechst 33258 from a non-selective topoisomerase (bacterial and human) inhibitor to a highly selective bacterial topoisomerase I inhibitor. Advantageously, The subject invention provides new approaches to targeting bacterial topoisomerases and the hydrophobic pocket in the DNA-E. coli topoisomerase I complex.

Reference is made to particular features (including method steps) of the invention. The disclosure of the invention in this specification should be understood to include all possible combinations of such particular features even if a particular combination is not specifically exemplified. For example, where a particular feature is disclosed in the context of a particular aspect or embodiment of the invention, that feature can also be used, to the extent possible, in combination with and/or in the context of other particular aspects and embodiments of the invention, and in the invention generally.

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

Reference is made to particular features (including method steps) of the invention. The disclosure of the invention in this specification should be understood to include all possible combinations of such particular features even if a particular combination is not specifically exemplified. For example, where a particular feature is disclosed in the context of a particular aspect or embodiment of the invention, that feature can also be used, to the extent possible, in combination with and/or in the context of other particular aspects and embodiments of the invention, and in the invention generally.

According to specific embodiments of the subject invention, bisbenzimidazoles (e.g., DPA 151-DPA 154), which are excellent inhibitors of E. coli DNA topoisomerase I, also display good antibacterial activity. Advantageously, the E. coli topoisomerase I inhibition is extremely selective, as DNA gyrase and mammalian topoisomerases are not inhibited. The E. coli. Topo I $IC_{50}$ (2.47±0.06 μM) for DPA 153 is even better than recently reported bisbenzimidazole derivative DMA (3.8 μM) (Bansal, S. et al., *Journal of Antimicrobial Chemotherapy* (2012) 67, 2882-2891). Without being bound by theory, the alkyl linkers present in the benzimdiazoles may interact with the bacterial topoisomerase I enzyme leading to a stabilization of the cleavable complex. The alkynyl chains may interact with the ternary complex as the bisbenzimidazole binds in the minor groove of DNA. The findings suggest that the ternary complex formed by the bacterial Topoisomerase I has distinct sites for recognition, as compared to those found in DNA gyrase and mammalian topoisomerases, and these differences can be further exploited for antibacterial drug development.

In one aspect, the present invention provides a compound of Formula (I):

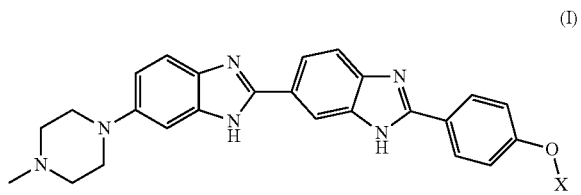

(I)

and salts and derivatives thereof, wherein X is a hydrophobic group.

In a specific embodiment, X comprises a terminal alkyne group attached through a hydrophobic linker to the oxygen.

Derivatives of the compounds described herein include any pharmaceutically acceptable ester, salt of an ester, alcohol, diol, ether, aldehyde, ketone, carboxylic acid, or enol of a compound that can be made from the compound by a chemical or physical process. Examples of derivatives include, but are not limited to the monobenzimidazole (instead of the bisbenzimidazole), the molecule with the piperzine removed, and the molecule with substituents on the aromatic rings. The substituents may be, for example, an alkyl, hydroxy, or any of the groups listed above.

Additional aspects of the present invention provide pharmaceutical compositions comprising therapeutically effective amounts of one or more of the compounds of Formula (I), and one or more pharmaceutically acceptable carriers and/or diluents. In some embodiments, the pharmaceutical compositions can also include additional active agents, such as antibiotic compounds, known in the art.

The compounds of the present invention can be represented, described, and/or applied for the purposes of the present invention in their pharmaceutically acceptable salt form. The compound, its salts, and derivatives may be hydrated or anhydrous. For instance, the compounds, salts, and derivatives can be in forms, such as, but not limited to, a solid, such as crystallized or powdered; or as a liquid, such as dissolved, disassociated, or solubilized in an appropriate solvent. As used herein, "compound" may also refer to the chemical and any associated ions, molecules, or atoms.

The compounds described herein are not to be limited to any particular stereochemical rendering, and include all stereochemical configurations. For example, the compounds of the present invention may contain one or more asymmetric centers or a non-aromatic double bond. Therefore, they can occur as racemates and racemic mixtures, single enantiomers, individual diastereomers, diastereomeric mixtures, and cis- or trans-isomeric forms. The compounds can also be dextrorotary (D) or levorotary (L). Moreover, each chiral center may be (S)- or (R)-. As such, it would be understood by those skilled in the art that the various forms of the compounds of the present invention would be encompassed by the present invention.

The composition may be an aqueous solution or a dry formulation. Furthermore, the composition may be in a sterile form. The compositions described herein may also be stored in a freeze-dried form and may be associated with stabilizing agents. As a dry formulation, the composition may further comprise other compounds, excipients, fillers, carriers (vehicles), and binders including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, whether an aqueous solution or a dry formulation, pharmaceutically acceptable carriers, excipients and binders contemplated for use in the practice of the present invention are those that are compatible with the active ingredient (i.e., active compound) and which render the compounds of the invention amenable to delivery, such as intravenous delivery, subcutaneous delivery, transcutaneous delivery, intracutaneous delivery, oral delivery, and the like; and bioavailability.

The term "pharmaceutically acceptable salt," as used herein, refer to the salts of the compounds of the present invention that are non-toxic. Suitable pharmaceutically acceptable salts of the compounds include acid addition salts which may, for example, be formed by mixing a solution of the compound with a solution of a pharmaceutically acceptable acid such as, but not limited to, hydrochloric acid, citric acid, benzoic acid, sulfuric acid, acetic acid, maleic acid, succinic acid, tartaric acid, carbonic acid, fumaric acid, or phosphoric acid. Furthermore, where the compounds of the invention carry an acidic moiety, suitable pharmaceutically acceptable salts thereof may include salts formed with suitable organic ligands, e.g., quaternary ammonium salts; alkali metal salts, e.g., sodium or potassium salts; and alkaline earth metal salts, e.g., calcium or magnesium salts. Therefore, representative pharmaceutically acceptable salts include, but are not limited to, the following: acetate, benzenesulfonate, benzoate, bicarbonate, bisulfate, carbonate, chloride, palmitate, citrate, dihydrochloride, glutamate, tartrate, teoclate, tosylate, glycollylarsanilate, hexylresorcinate, hydrabamine, hydrobromide, iodide, methylnitrate, methylsulfate, mucate, napsylate, nitrate, N-methylglucamine ammonium salt, oleate, pamoate, pantothenate, edetate, edisylate, estolate, lactate, esylate, fumarate, gluceptate, hydrochloride, hydroxynaphthoate, mandelate, mesylate, bromide, calcium edetate, camsylate, subacetate, succinate, tannate, gluconate, phosphate/diphosphate, isothionate, lactobionate, laurate, malate, maleate, methylbromide, clavulanate, polygalacturonate, salicylate, stearate, sulfate, bitartrate, borate, triethiodide and valerate.

Reference is made to particular features (including method steps) of the invention. The disclosure of the invention in this specification should be understood to include all possible combinations of such particular features even if a particular combination is not specifically exemplified. For example, where a particular feature is disclosed in the context of a particular aspect or embodiment of the invention, that feature can also be used, to the extent possible, in combination with and/or in the context of other particular aspects and embodiments of the invention, and in the invention generally.

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

Reference is made to particular features (including method steps) of the invention. The disclosure of the invention in this specification should be understood to include all possible combinations of such particular features even if a particular combination is not specifically exemplified. For example, where a particular feature is disclosed in the context of a particular aspect or embodiment of the invention, that feature can also be used, to the extent possible, in combination with and/or in the context of other particular aspects and embodiments of the invention, and in the invention generally.

In one embodiment of the compound of Formula (I), the compound is 6-(4-methylpiperazin-1-yl)-2'-(4-(prop-2-ynyloxy)phenyl)-1H,3'H-2,5'-bibenzo[d]imidazole (termed DPA 151), which is represented by the Formula (Ia):

(Ia)

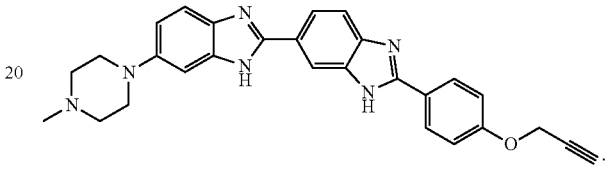

In another embodiment of the compound of Formula (I), the compound is 2'-(4-(hex-5-ynyloxy)phenyl)-6-(4-methylpiperazin-1-yl)-1H,3'H-2,5'-bibenzo[d]imidazole (termed DPA 152), which is represented by the Formula (Ib):

(Ib)

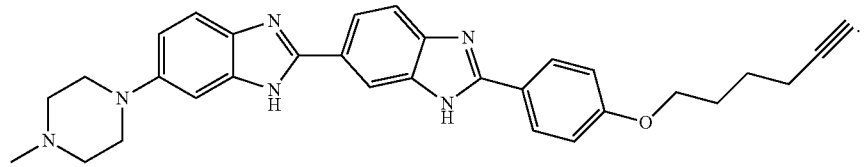

In another embodiment of the compound of Formula (I), the compound is 6-(4-methylpiperazin-1-yl)-2'-(4-(undec-10-ynyloxy)phenyl)-1H,3'H-2,5'-bibenzo[d]imidazole (termed DPA 153), which is represented by the Formula (Ic):

(Ic)

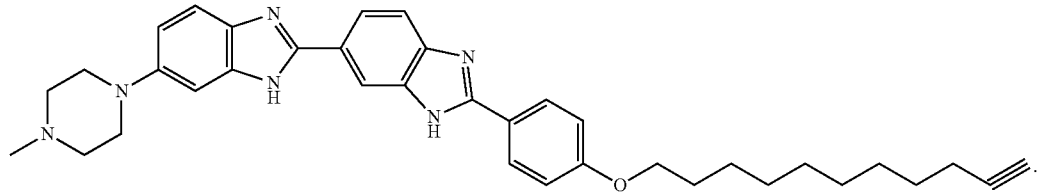

In another embodiment of the compound of Formula (I), the compound is 6-(4-methylpiperazin-1-yl)-2'-(4-(4-(prop-2-ynyloxy)butoxy)phenyl)-1H,3'H-2,5'-bibenzo[d]imidazole (termed DPA 154), which is represented by the Formula (Id):

(Id)

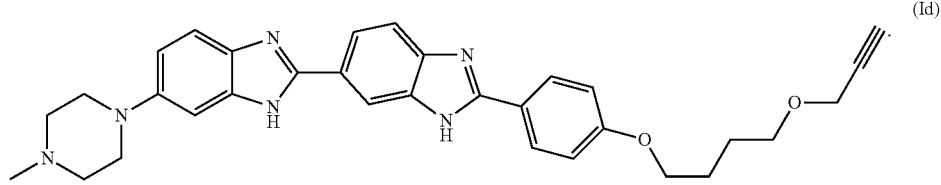 [SMILES: C#CCOCCCCOc1ccc(-c2nc3ccc(-c4nc5ccc(N6CCN(C)CC6)cc5[nH]4)cc3[nH]2)cc1]

The present invention further provides methods for treating bacterial infections in subjects in need thereof, comprising administering a therapeutically effective amount of one or more of the compounds of Formula (I). The compounds described herein have effective anti-microbial activity and are selective for bacterial topoisomerase I inhibition. In some embodiments, the compounds of the present invention target and inhibit bacterial topoisomerase I of E. coli.

In additional embodiments, the methods for treating bacterial infections in subjects in need thereof comprise administering a therapeutically effective amount of one or more of the compounds of Formula (I) along with one or more additional antibiotics. Additional antibiotics may include, but are not limited to, beta-lactams, macrolides, tetracyclines, quinolones, aminoglycosides, sulfonamides, glycopeptides, and oxazolidinones.

As used herein, the term "subject" refers to any animal (e g, mammals, birds, reptiles, amphibians, fish), including, but not limited to, humans, non-human primates, rodents, and the like, which is to be the recipient of a particular treatment.

Furthermore, it would be understood by those skilled in the art that the therapeutic methods described would not only apply to treatment in a subject, but could be applied to cell cultures, organs, tissues, or individual cells in vivo, ex vivo or in vitro, including tumors, cancers and immortalized cells isolated or derived from a subject.

Typically, the terms "subject" and "patient" may be used interchangeably herein in reference to a subject. Furthermore, transgenic animals (e.g., transgenic rats and mice) are useful in the methods of the present invention.

As used herein, the term "administering" refers to providing or delivering a therapeutically effective amount of a chemical compound or pharmaceutical composition to a subject or location, using intravenous, subcutaneous, transcutaneous, intracutaneous, oral, and the like administration. The compounds of the subject invention can also be used for disinfecting surfaces. The chemical compound of the present invention can be administered alone, but may be administered with other pharmaceutically acceptable compounds, excipients, fillers, binders, or carriers (vehicles) selected based upon the chosen route of administration and standard pharmaceutical practice. Administration may be by way of carriers or vehicles, such as injectable solutions, including sterile aqueous or non-aqueous solutions, or saline solutions; capsules; tablets; granules; pellets; powders; suspensions or emulsions or microemulsions; patches; micelles; liposomes; vesicles; implants, including microimplants; synthetic polymers; microspheres; nanoparticles; and the like.

The terms "effective amount" and "therapeutically effective amount" may be used interchangeably, and as applied to the compounds and pharmaceutical compositions herein, mean the quantity necessary to effect the desired antibacterial result. For example, an effective amount is a level effective to treat, cure, or alleviate the symptoms of a disorder for which the therapeutic compound or composition is being administered. Amounts effective for the particular therapeutic goal sought will depend upon a variety of factors including the disorder being treated and its severity; the activity of the specific compound or pharmaceutical composition used; the route of administration; the rate of clearance of the specific compound; the duration of treatment; treatment regimen; the drugs used in combination or coincident with the specific compound or composition; the age, body weight, sex, diet, physiology and general health of the subject being treated; and like factors well known to one of skill in the relevant scientific art. Some variation in dosage will necessarily occur depending upon the condition of the subject being treated, and the physician will, in any event, determine the appropriate dose for the individual subject, e.g., patient. Generally, an effective amount is a dosage that kills bacterial cells and alleviates any symptoms caused by the bacterial infection on/in the subject.

Aspects of the present invention also include kits comprising the compounds and pharmaceutical compositions as described herein. The kits may further be used in the methods described herein. The kits may also include at least one reagent and/or instructions for their use. Also, the kit may include one or more containers filled with reagent(s) and/or one or more components of the pharmaceutical compositions of the invention. One or more container of the kits provided may also comprise a compound of the invention, preferably in a purified form. The kits may also comprise a control composition, such as a control antibiotic.

Reference is made to particular features (including method steps) of the invention. The disclosure of the invention in this specification should be understood to include all possible combinations of such particular features even if a particular combination is not specifically exemplified. For example, where a particular feature is disclosed in the context of a particular aspect or embodiment of the invention, that feature can also be used, to the extent possible, in combination with and/or in the context of other particular aspects and embodiments of the invention, and in the invention generally.

The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

EXAMPLES

The methods and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented.

The following Materials and Methods were used for all the methods and compositions exemplified herein.

General Methods

Unless otherwise specified, chemicals were purchased from Aldrich (St. Louis, Mo.) or Fisher Scientific (Pittsburgh, Pa.) and used without further purification. Hoechst 33258 and Hoechst 33242 were obtained as their hydrochloride salts and used without further purification. All solvents were purchased from VWR (West Chester, Pa.). Silica gel (32-65 μM mesh size) was purchased from Sorbtech (Atlanta, Ga.). $^1$H NMR and $^{13}$C NMR spectra were recorded on a Bruker Avance (300/500 MHz) Spectrometer. Chemical shift is given in ppm and referenced to residual solvent peaks ($^1$H and $^{13}$C NMR). Mass (MALDI-TOF) spectra were collected using a Bruker Microflex mass spectrometer. Ultra Violet (UV) spectra were collected on a Varian (Walnut

Synthesis

Synthesis of 4-(prop-2-ynyloxy)benzaldehyde (DPA 151a)

To a solution of p-hydroxybenzaldehyde (2.00 g, 16.3 mmol) in dry dichloromethane (30.0 mL) and 1, 4 dioxane (5.00 mL), triphenyl phosphine (6.30 g, 24.2 mmol) and propargyl alcohol (0.91 g, 16.3 mmol) were dissolved under argon and the solution was ice cooled. To this mixture, diisopropyl azodicarboxylate (DIAD) (4.80 mL, 24.2 mmol) was added dropwise over a period of 15 minutes at 0° C. The contents were initially stirred at 0° C. for 30 minutes and then allowed to slowly warm up to room temperature and stirred overnight. Progress of the reaction was monitored using thin layer chromatography (TLC) on silica gel. The volatiles were removed under reduced pressure and the gummy residue was redissolved in ethyl acetate-hexane (80.0 mL, 1:1 v/v). The reaction mixture was allowed to stand overnight in the refrigerator. The precipitated solid was vacuum filtered and the filtrate was concentrated under reduced pressure. The crude product was purified by column chromatography on silica gel (hexanes-ethyl acetate, 100:0-70:30) to afford the desired compound as a white solid (1.3 g, 50%): $R_f$=0.42 (hexanes:ethyl acetate 7:3 v/v); mp 80-81° C.; IR (neat, cm$^{-1}$) 3419, 2112, 1654; $^1$H NMR (500 MHz, CDCl$_3$) δ 9.91 (s, 1H), 7.87 (dd, $J_1$=8.82 Hz, $J_2$=1.94 Hz, 2H), 7.10 (dd, $J_1$=8.74 Hz, $J_2$=1.70 Hz, 2H), 4.77 (d, J=2.36 Hz, 2H, —OCH$_2$CCH), 2.60 (t, J=2.43 Hz, 1H, —OCH$_2$CCH); $^{13}$C NMR (125 MHz, CDCl$_3$) δ 190.7, 162.3, 131.8, 130.6, 115.1, 77.8, 76.3, 55.9.

Synthesis of N-methoxy-N-methyl-2-(4-(prop-2-ynyloxy)phenyl)-1H-benzo[d]imidazole-6-carboxamide (DPA 151-b)

To a solution of N-Methoxy, N-methyl 3, 4 dinitrobenzamide (0.90 g, 3.52 mmol) in ethanol (20.0 mL), 150 mg of 10% Pd—C was added. Hydrogenation for 5 h at the atmospheric pressure afforded corresponding diamine. The diamine was used immediately after filtration of the catalyst without further purification. 4-(prop-2-ynyloxy)benzaldehyde (0.62 g, 3.87 mmol) and sodium metabisulfite (0.37 g, 1.93 mmol) in water (1.00 mL) were added into the diamine and the reaction mixture was refluxed for 12 h. The volatiles were evaporated under reduced pressure. The crude product was purified by column chromatography on silica gel using dichloromethane-methanol (0-10% methanol in dichloromethane) as eluent to afford the desired product as a pale yellow solid (0.55 g, 83%): $R_f$=0.53 (dichloromethane:methanol 9:1, v/v); mp 245-246° C.; IR (neat, cm$^{-1}$) 2974, 2124, 1617; $^1$H NMR (500 MHz, DMSO-d$_6$) δ 13.1 (s, 1H), 8.15 (d, J=8.5 Hz, 2H), 7.91-7.79 (m, 1H), 7.67 (d, J=8.50 Hz, 1H, 7.55 (d, J=8.00 Hz, two sets of doublets, 1H), 7.50-7.46 (m, 1H), 7.18 (dd, $J_1$=2.50 Hz, $J_2$=9.00 Hz, 2H), 4.92 (d, J=2.53 Hz, 2H, —OCH$_2$CCH), 4.36 (d, J=2.12 Hz, 1H, —OCH$_2$CCH), 3.58 (s, 3H), 3.35 (s, 3H); $^{13}$C NMR (125 MHz, DMSO-d$_6$) δ 170.1, 169.9, 159.4, 159.3, 153.6, 153.1, 145.9, 137.0, 128.6, 123.1, 119.0, 115.8, 111.0, 79.0, 62.5, 56.1, 25.9; MS (MALDI-TOF) m/z calcd for $C_{19}H_{17}N_3O_3$ 335.13. found 336.38 [M+H]$^+$.

Synthesis of 2-(4-(prop-2-ynyloxy)phenyl)-1H-benzo[d]imidazole-6-carbaldehyde (DPA 151-c)

To a solution of N-methoxy-N-methyl-2-(4-(prop-2-ynyloxy)phenyl)-1H-benzo[d]imidazole-6-carboxamide (0.30 g, 0.89 mmol) in tetrahydrofuran (THF)-ether (40 mL, 3:1 v/v), lithium aluminum hydride (0.13 g, 3.57 mmol) was added in small portions at −70° C. under argon and then the stirring was continued for 6 hours while allowing the slush bath to warm up to −20° C. The reaction mixture was quenched by the addition of saturated ammonium chloride solution (50 mL). The precipitated grey solid was filtered off. The filtrate was extracted with ethyl acetate (3×50 mL). Organic layers were combined and then dried over sodium sulfate. Volatiles were removed under reduced pressure. The crude product was purified by column chromatography on silica gel using hexanes:ethyl acetate (1:1-2:1 v/v) to yield the desired compound as a light yellow solid (0.18 g, 73%): $R_f$=0.76 (in ethyl acetate); mp>255° C. (dec); IR (neat, cm$^{-1}$) 3278, 2919, 2120, 1669; $^1$H NMR (500 MHz, DMSO-d$_6$) δ 13.25 (s, br, 1H), 10.05 (s, 1H), 8.18 (d, J=8.50 Hz, 2H), 8.10 (br, 1H), 7.77 (br, 1H) 7.68 (br, 1H) 7.20 (d, J=9.0 Hz, 2H), 4.92 (d, J=2.66 Hz, 2H, —OCH$_2$CCH), 3.65 (t, J=2.28 Hz, 1H, —OCH$_2$CCH); $^{13}$C NMR (125 MHz, DMSO-d$_6$) δ 193.0, 159.6, 155.4, 154.1, 149.0, 144.2, 135.5, 131.5, 129.0, 123.4, 119.3, 115.8, 114.2, 112.2, 79.4, 60.2, 56.1; MS (MALDI-TOF) m/z calcd for $C_{17}H_{12}N_2O_2$ [M]$^+$ 276.09. found 277.66 ([M+H]$^+$).

Synthesis of 6-(4-methylpiperazin-1-yl)-2'-(4-(prop-2-ynyloxy)phenyl)-1H,3'H-2,5'-bibenzo[d]imidazole (DPA 151)

To a solution of 5-(4-methylpiperazin-1-yl)-2-nitroaniline (0.06 g, 0.27 mmol) in ethanol (8.0 mL), 10% Pd—C (40.0 mg) was added and then it was hydrogenated for 6 hours at the atmospheric pressure. TLC on silica gel (ethyl acetate-methanol 8:2 v/v) showed complete reduction of the starting material. After filtering the catalyst over a bed of celite, 2-(4-(prop-2-ynyloxy)phenyl)-3H-benzoimidazole-5-carbaldehyde (0.08 g, 0.31 mmol) was added. To this solution, Na$_2$S$_2$O$_5$ (30.0 mg, 0.16 mmol) in water (0.2 mL) was added and the mixture was refluxed for 14 hours. The reaction mixture was allowed to come to the room temperature. The volatiles were evaporated under reduced pressure. The crude product was purified by column chromatography on silica gel using dichloromethane-methanol as eluent (0-18% methanol in dichloromethane) to afford the desired product as yellow solid (85 mg, 65%): $R_f$=0.23 (ethyl acetate-methanol 8:2 v/v); mp 252-256° C.; IR (neat, cm$^{-1}$) 3235, 2919, 2109; $^1$H NMR (300 MHz, methanol-d$_4$) δ 8.25 (br, 1H), 8.06 (d, J=8.84 Hz, 2H), 7.95 (dd, $J_1$=9.97 Hz, $J_2$=1.30 Hz, 1H), 7.69 (d, J=8.32 Hz, 1H), 7.51 (d, J=8.77 Hz, 1H), 7.15 (3H), 7.05 (s, 1H), 4.82 (d, J=2.29 Hz, 2H), 3.24 (t, J=4.55 Hz, 4H), 3.04 (t, J=2.33 Hz, 1H), 2.72 (t, J=4.64 Hz, 4 Hz), 2.42 (s, 3H) (some proton peaks are masked with the solvent peaks); $^{13}$C NMR (75 MHz, DMSO-d$_6$) δ 159.1, 153.2, 152.1, 145.3, 144.5, 138.6, 136.4, 135.7, 128.6, 123.5, 122.0, 120.7, 119.1, 116.5, 115.7, 111.9, 97.6, 79.4, 79.0, 56.0, 55.3, 50.7 50.2, 46.2; ESI-HRMS (m/z) calcd. for $C_{28}H_{27}N_6O$, 462.2246. found 463.2237.

Synthesis of 4-(hex-5-ynyloxy)benzaldehyde (DPA 152-a)

To an ice cold solution of p-hydroxy benzaldehyde (1.00 g, 8.18 mmol) in dry dichloromethane (15.0 mL) and dioxane (5.0 mL), 5-Hexyn-1-ol (0.80 g, 8.18 mmol) and triphenyl phosphine (3.17 g, 12.1 mmol) were added under argon. To this solution, DIAD (2.40 mL, 12.1 mmol) was added dropwise. The reaction mixture was stirred at 0° C. for 1 hour followed by stirring at room temperature for 6 hours.

Volatiles were evaporated and the crude mixture was redissolved in ethyl acetate-hexanes (80.0 mL, 1:1 v/v). The mixture was allowed to stand in the refrigerator for a day and the precipitated solid was vacuum filtered. The filtrate containing the crude product was concentrated under reduced pressure. The crude mixture was purified on a silica gel column using hexanes-ethyl acetate (0-25% ethyl acetate in hexanes) as eluent to yield the desired compound as colorless oil (1.4 g, 85%): $R_f$=0.7 (hexanes-ethyl acetate 7:3); $^1$H NMR (300 MHz, CDCl$_3$) δ 9.81 (s, 1H), 7.82 (dd, J$_1$=8.82 Hz, J$_2$=1.98 Hz, 2H), 7.00 (dd, J$_1$=8.71 Hz, J$_2$=1.75 Hz, 2H), 4.08 (d, J=6.25 Hz, 2H, —OCH$_2$CCH), 2.32-2.27 (m, 2H), 2.00-1.91 (m, 3H), 1.79-1.69 (m, 2H); $^{13}$C NMR (125 MHz, CDCl$_3$) δ 190.8, 164.1, 132.0, 130.7, 114.7, 84.8, 68.8, 67.7, 28.0, 24.8, 18.1.

Synthesis of 2-(4-(hex-5-ynyloxy)phenyl)-N-methoxy-N-methyl-3H-benzoimidazole-5-carboxamide (DPA 152-b)

To a solution of N-Methoxy, N-methyl 3, 4 dinitrobenzamide (1.00 g, 3.91 mmol) in ethanol (30.0 mL), 10% Pd—C (0.10 g) was added. Hydrogenation for 5 hours at atmospheric pressure yielded corresponding diamine which was used immediately after filtration of the catalyst. 4-(hex-5-ynyloxy)benzaldehyde (0.82 g, 4.10 mmol) and sodium metabisulfite (0.39 g, 2.05 mmol) in water (0.50 mL) were added into it. The reaction mixture was refluxed for 8 h. Volatiles were evaporated under reduced pressure. Column chromatography on silica gel using dichloromethane-methanol (0-8% methanol in dichloromethane) as eluent afforded the desired product as pale brown oil (1.1 g, 74%): $R_f$=0.75 (in dichloromethane-isopropanol 9:1 v/v); IR (neat, cm$^{-1}$) 3297 (alkyne C—H stretch), 2938 (aromatic C—H stretch), 2116 (alkyne C—C stretch), 1723; $^1$H NMR (300 MHz, DMSO-d$_6$) δ 8.13 (d, br, J=13.7 Hz, 2H), 7.93-7.80 (1H), 7.67 (dd, J$_1$=8.27 Hz, J$_2$=8.36 Hz, 1H), 7.48 (d, J=8.62 Hz, 1H), 7.11 (d, br, J=8.87 Hz, 2H), 4.07 (t, J=4.64 Hz, 2H, —OCH$_2$CCH), 3.57 (s, 3H), 3.30 (s, 3H), 2.80 (t, J=2.64 Hz, 1H, —OCH$_2$CCH), 2.28-2.22 (m, 2H), 1.88-1.79 (m, 2H), 1.67-1.57 (m, 2H) (Imino proton was not observed); $^{13}$C NMR (75 MHz, DMSO-d$_6$) δ 170.2, 160.7, 153.8, 146.0, 143.4, 137.0, 128.7, 123.0, 119.0, 115.3, 111.8, 84.7, 71.8, 67.6, 60.9, 34.1, 28.2, 25.0, 21.1, 17.9; MS (MALDI-TOF) m/z calcd. for C$_{22}$H$_{23}$N$_3$O$_3$ [M]$^+$ 377.17. found 378.34 [M+H]$^+$.

Synthesis of 2-(4-(hex-5-ynyloxy)phenyl)-3H-benzimidazole-5-carbaldehyde (DPA 152-c)

To a stirred suspension of 2-(4-(hex-5-ynyloxy)phenyl)-N-methoxy-N-methyl-3H-benzoimidazole-5-carboxamide (0.77 g, 2.04 mmol) in dry THF (40.0 mL), lithium aluminum hydride (0.31 g, 8.17 mmol) was added in small portions at −70° C. under argon and the stirring was continued for 12 hours at 0° C. TLC was used to monitor the progress of the reaction. The reaction mixture was quenched by the addition of saturated ammonium chloride solution (100 mL). The resulting grey precipitate was filtered off. The filtrate was extracted by ethyl acetate (3×100 mL). Organic layers were combined and dried over sodium sulfate. Volatiles were removed under reduced pressure. Column chromatography on silica gel using hexanes-ethyl acetate (1:1-2:1) as eluent afforded the desired compound as light yellow liquid (0.47 g, 72%): $R_f$=0.66 (ethyl acetate:hexanes 6:4 v/v); mp 156-158° C.; IR (neat, cm$^{-1}$) 3289 (alkyne C—H stretch 2116 (alkyne C—C stretch), 1696; $^1$H NMR (300 MHz, methanol-d$_4$) δ 13.20 (br, 1H), 9.89 (s, 1H), 7.96 (br, 1H) 7.87 (dd, J$_1$=8.89 Hz, J$_2$=2.01 Hz, 2H), 7.69 (dd, J$_1$=9.8 Hz, J$_2$=1.44 Hz, 1H), 7.56 (d, J=8.32 Hz, 1H), 6.91 (dd, J$_1$=8.92 Hz, J$_2$=2.02 Hz, 2H), 3.93-3.89 (t, J=5.91 Hz, 2H, —OCH$_2$CCH), 2.25-2.20 (m, 3H), 1.88-1.79 (m, 2H), 1.69-1.59 (m, 2H); $^{13}$C NMR (75 MHz, DMSO-d$_6$) δ 192.4, 171.5, 161.5, 155.2, 131.7, 128.3, 123.7, 121.0, 114.6, 83.3, 68.5, 67.4, 60.1, 27.9, 24.8, 19.9, 17.4, 16.5; MS (MALDI-TOF) m/z calcd. for C$_{20}$H$_{18}$N$_2$O$_2$ [M]$^+$ 318.14. found 319.25 [M+H]$^+$.

Synthesis of 2'-(4-(hex-5-ynyloxy)phenyl)-6-(4-methylpiperazin-1-yl)-1H,3'H-2,5'-bibenzo[d]imidazole (DPA 152)

To a solution of 5-(4-methylpiperazin-1-yl)-2-nitroaniline (0.28 g, 1.00 mmol) in ethanol (40.0 mL), Pd—C (0.10 g) was added which was followed by hydrogenation at atmospheric pressure for 5 hours. Charcoal was filtered off over a bed of celite. To this solution, 2-(4-(hex-5-ynyloxy)phenyl)-3H-benzimidazole-5-carbaldehyde (0.35 g, 1.10 mmol) and a solution of Na$_2$S$_2$O$_5$ (0.10 g, 0.55 mmol) in water (0.20 mL) were added and the mixture was refluxed for 23 hours. The reaction mixture was allowed to come to room temperature. The filtrate was evaporated under reduced pressure. Column chromatography on silica gel using dichloromethane-methanol as eluent (0-15% methanol in dichloromethane) afforded the desired product as yellow solid (0.36 g, 72%): $R_f$=0.15 (ethyl acetate:methanol 8:2 with two drops of triethylamine); mp 210-220° C.; IR (neat, cm$^{-1}$) 3293 (alkyne C—H stretch), 2116 (alkyne C—C stretch), 1618; $^1$H NMR (500 MHz, methanol-d$_4$) δ 8.21 (s, 1H), 8.00 (dd, J$_1$=8.60 Hz, J$_2$=2.06 Hz, 2H), 7.92 (dd, J$_1$=8.64 Hz, J$_2$=2.02 Hz, 1H) 7.66 (d, J=8.30 Hz, 1H), 7.51 (d, J=9.00 Hz, 1H), 7.12 (d, J=8.80 Hz, 1H), 7.04 (d, J=8.54 Hz, 1H), 7.02 (dd, J$_1$=8.84 Hz, J$_2$=2.06 Hz, 2H), 4.01 (t, J=2.26 Hz, 2H, —OCH$_2$CCH), 3.24 (t, J=4.62 Hz, 4H), 2.75 (t, J=4.66 Hz, 4H), 2.53 (s, br, 1H), 2.44 (s, 3H), 2.28-2.24 (m, br, 2H), 1.93-1.86 (m, br, 2H), 1.70-1.77 (m, br, 2H) (Imino protons were not observed because of exchange with the NMR solvent); ESI-HRMS (m/z) calcd. for C$_{31}$H$_{33}$N$_6$O, 505.2716. found 505.2701; HPLC: t$_R$ 2.87 min, purity 96.1% (see procedure for method details).

Synthesis of 4-(undec-10-ynyloxy)benzaldehyde (DPA153-a)

To an ice cold solution of p-hydroxybenzaldehyde (0.50 g, 4.09 mmol) in dry dichloromethane-dioxane mixture (15.0 mL 2:1 v/v), triphenyl phosphine (1.60 g, 6.05 mmol) and 10-undecyn-1-ol (0.70 g, 6.05 mmol) were dissolved and kept at 0° C. To this, diisopropyl azodicarboxylate (1.22 g, 6.05 mmol) was added dropwise over a period of 15 minutes. The contents were initially stirred at 0° C. for 30 minutes and then allowed to warm up to room temperature and stirred overnight. The crude mixture was concentrated and redissolved in ethyl acetate-hexanes mixture (50 mL, 1:1 v/v) and kept in the refrigerator for a day. The precipitated solid was filtered off and the filtrate was concentrated under reduced pressure. Column chromatography on silica gel using hexanes-ethyl acetate as eluent (0-50% ethyl acetate in hexanes) afforded the desired compound as white solid (0.58 mg, 52%): $R_f$=0.54 (hexanes-ethyl acetate 7:3 v/v); mp 65-68° C.; IR (neat, cm$^{-1}$) 3421 (alkyne C—H stretch), 2097 (alkyne C—C stretch), 1684; $^1$H NMR (300 MHz, CDCl$_3$) δ 9.90 (s, 1H), 7.84 (dd, J$_1$=7.1 Hz, J$_2$=1.9 Hz, 2H), 7.00 (dd, J$_1$=7.1 Hz, J$_2$=1.9 Hz, 2H), 4.06 (t, J=6.50 Hz, 2H, —OCH$_2$CCH), 2.23-2.18 (m, 2H), 1.96 (t, J=2.71 Hz, 1H, —OCH$_2$CCH), 1.88-1.79 (m, 2H), 1.58-1.27 (12H); $^{13}$C NMR (125 MHz, CDCl$_3$) δ 190.8, 164.2, 131.9, 129.7, 114.7, 84.7, 74.3 68.4, 68.1, 29.3, 29.1, 29.0, 28.7 28.4, 21.6, 18.4.

Synthesis of N-methoxy-N-methyl-2-(4-(undec-10-ynyloxy)phenyl)-1H-benzo[d]imidazole-6-carboxamide (DPA 153-b)

To a solution of N-Methoxy, N-methyl 3, 4 dinitrobenzamide (0.40 g, 1.37 mmol) in ethanol-ethyl acetate mixture (15.0 mL), 10% Pd—C (0.09 g) was added. Hydrogenation at atmospheric pressure for 5 hours afforded corresponding diamine which was used without purification after filtration of the catalyst. 4-(undec-10-ynyloxy)benzaldehyde (0.49 g, 1.78 mmol) and sodium metabisulfite (0.26 g, 1.37 mmol) in water (1.00 mL) were added into it and the reaction mixture was refluxed overnight. Volatiles were evaporated under reduced pressure. The crude product was purified on a silica gel column using dichloromethane-methanol (0-10% methanol in dichloromethane) as eluent to afford the desired product as slightly yellow gummy solid (0.60 g, 85%): R$_f$=0.67 (dichloromethane-isopropanol 9:1 v/v); IR (neat, cm$^{-1}$) 3305 (alkyne C—H stretch), 2112 (alkyne C—C stretch), 1614; $^1$H NMR (300 MHz, acetone-d$_6$) δ 8.17 (d, J=8.4 Hz, 2H), 8.03-7.87 (br, 1H), 7.68-7.50 (m, 2H), 7.11 (d, J=8.7 Hz, 2H), 4.14 (t, J=6.2 Hz, 2H, —OCH$_2$CCH), 3.62 (s, 3H), 3.34 (s, 3H), 2.32 (t, J=2.5 Hz, 1H, —OCH$_2$CCH), 2.21-2.16 (m, 2H), 1.88-1.78 (m, 2H), 1.57-1.30 (m, 12H) (Imino proton was not observed because of exchange with the NMR solvent); $^{13}$C NMR (75 MHz, acetone-d$_6$) δ 170.1, 160.9, 153.4, 138.9, 137.2, 128.3, 128.2, 122.7, 122.4, 118.2, 117.5, 114.7, 113.8, 101.2, 84.1, 68.9, 67.9, 60.2, 33.3, 29.7-28.2 (peaks masked with the acetone-d$_6$ peak), 25.8, 27.8; MS (MALDI-TOF) m/z calcd. for C$_{27}$H$_{33}$N$_3$O$_3$ 447.57. found 448.69 ([M+H]$^+$).

Synthesis of 2-(4-(undec-10-ynyloxy)phenyl)-1H-benzo[d]imidazole-6-carbaldehyde (DPA 153-c)

To a solution of N-methoxy-N-methyl-2-(4-(undec-10-ynyloxy)phenyl)-1H-benzo[d]imidazole-6-carboxamide (0.80 g, 1.78 mmol) in THF-ether (80.0 mL, 3:1), lithium aluminum hydride (0.20 g, 5.28 mmol) was added at −78° C. under argon and then allowed to stir at 0° C. for 8 hours. The reaction mixture was quenched by the addition of saturated ammonium chloride solution (75.0 mL). The resulting grey precipitate was filtered off. The filtrate was extracted with ethyl acetate (3×100 mL). Organic layers were combined and dried over sodium sulfate. Volatiles were removed under reduced pressure. Column chromatography on silica gel using hexanes-ethyl acetate as eluent afforded the desired compound as a light yellow solid (0.42 g, 60%): R$_f$=0.78 (ethyl acetate-hexanes 6:4); mp 126-128° C.; IR (neat, cm$^{-1}$) 3305 (alkyne C—H stretch, 2108 (alkyne C—H stretch), 1503; $^1$H NMR (300 MHz, acetone-d$_6$) δ 10.08 (s, 1H), 8.20 (d, J=8.8 Hz, 2H), 8.14 (1H), 7.80 (dd, J$_1$=8.3 Hz, J$_2$=1.3 Hz, 1H), 7.72 (d, J=8.3 Hz, 1H), 7.11 (d, J=8.9 Hz, 2H), 4.10 (t, J=6.5 Hz, 2H, —OCH$_2$CCH), 2.32 (t, J=2.7 Hz, 1H, —OCH$_2$CCH), 2.21-2.15 (m, 2H), 1.87-1.78 (m, 2H), 1.56-1.37 (m, 12H) (Imino proton was not observed because of exchange with the NMR solvent); $^{13}$C NMR (125 MHz, acetone-d$_6$) δ 191.5, 161.3, 155.3, 154.0, 149.3, 144.5, 139.7, 138.9, 135.3, 131.8, 128.4, 127.9, 123.3, 122.1, 119.0, 114.9, 113.7, 112.9, 111.3, 84.0, 68.8, 67.9, 33.5, 28.1; MS (MALDI-TOF) m/z calcd. for C$_{25}$H$_{28}$N$_2$O$_2$ 388.50. found 390.12 ([M+2H]$^+$).

Synthesis of 6-(4-methylpiperazin-1-yl)-2'-(4-(undec-10-ynyloxy)phenyl)-1H,3'H-2, 5'-bibenzo[d]imidazole (DPA 153)

To a solution of 5-(4-methylpiperazin-1-yl)-2-nitroaniline (0.24 g, 1.02 mmol) in ethanol-ethyl acetate mixture (30.0 mL), 10% Pd—C (0.10 g) was added followed by hydrogenation at atmospheric pressure for 5 hours. TLC on silica gel showed complete reduction of the starting material. Charcoal was filtered over a bed of celite. To the filtrate, 2-(4-(undec-10-ynyloxy)phenyl)-1H-benzo[d]imidazole-6-carbaldehyde (0.40 g, 1.02 mmol) and a solution of Na$_2$S$_2$O$_5$ (0.19 g, 1.02 mmol) in water (1.0 mL) was added and the mixture was refluxed for 14 h. Volatiles were removed under reduced pressure. Column chromatography on silica gel in dichloromethane-methanol (0-15% methanol in dichloromethane) afforded the pure product as yellow solid (0.29 g, 50%): R$_f$=0.32 (dichlromethane-methanol 8:2); mp 170-175° C.; IR (neat, cm$^{-1}$) 2919 (aromatic C—H stretch), 1614; $^1$H NMR (300 MHz, methanol-d$_4$) δ 8.20 (br, 1H), 7.95-7.89 (br, 3H), 7.63 (d, J=8.5 Hz, 1H), 7.50 (d, J=8.7 Hz, 1H), 7.10 (d, J=2.0 Hz, 1H), 7.01 (dd, J$_1$=8.8 Hz, J$_2$=2.2 Hz, 1H), 6.93 (d, J=8.5 Hz, 2H), 3.85 (t, J=6.2 Hz, 2H), 3.21 (t, J=4.5 Hz, 4H), 2.72 (t, J=4.8 Hz, 4H), 2.42 (s, 3H), 2.19-2.11 (m, br, 3H), 1.73-1.63 (m, 2H), 1.52-1.22 (br, 12H) (Imino protons were not observed because of exchange with the NMR solvent); $^{13}$C NMR (75 MHz, DMSO-d$_6$) δ 160.7, 153.1, 148.0, 145.4, 144.6, 139.3, 136.5, 135.7, 128.6, 124.7, 122.6, 120.7, 119.0, 115.3, 115.1, 111.8, 85.02, 71.5, 71.5, 68.1, 61.5, 55.2, 46.0, 33.6, 29.3, 29.2, 29.1, 28.9, 28.5, 28.4, 25.9, 18.1; ESI-HRMS (m/z) calcd. for C$_{36}$H$_{43}$N$_6$O, 575.3498. found 565.3497; HPLC: t$_R$ 8.04 min, purity 98.4% (see procedure for method details).

Synthesis 4-(4-(prop-2-ynyloxy)butoxy)benzaldehyde (DPA 154-a)

To a solution of p-hydroxybenzaldehyde (4.00 g, 32.7 mmol) in dry dichloromethane-dioxane (40.0 mL, 3:1 v/v), triphenyl phosphine (12.6 g, 48.0 mmol) and 4-(prop-2-ynyloxy) butan-1-ol (4.20 g, 32.7 mmol) were dissolved and the solution was ice cooled. To this mixture, diisopropyl azodicarboxylate (9.70 g, 48.0 mmol) was added drop wise over a period of 15 minutes at 0° C. The contents were initially stirred at 0° C. for 30 minutes and then at room temperature overnight. The solvents were removed under reduced pressure and the mixture was redissolved in ethyl acetate-hexanes (100 mL, 1:1 v/v) and allowed to stand in the refrigerator overnight. The precipitated solid was filtered off and the filtrate was concentrated under reduced pressure. Column chromatography on silica gel using hexanes-ethyl acetate as eluent, afforded the desired compound as pale yellow oil (6.2 g, 82%): R$_f$=0.55 (hexanes-ethyl acetate 7:3 v/v); IR (neat, cm$^{-1}$) 3289 (alkyne C—H stretch), 2116 (alkyne C—C stretch), 1688; $^1$H NMR (500 MHz, CDCl$_3$) δ 9.84 (s, 1H), 7.79 (dd, J$_1$=1.79 Hz, J$_2$=8.81 Hz, 2H), 6.96 (d, J=8.81 Hz, 2H), 4.13 (d, J=2.39 Hz, 2H), 4.04 (t, J=6.27 Hz, 2H), 3.57 (t, J=6.42 Hz, 2H), 2.45 (t, J=2.38 Hz, 1H), 1.92-1.87 (m, 2H), 1.79-1.74 (m, 2H); $^{13}$C NMR (125 MHz, CDCl$_3$) 190.7, 164.1, 131.9, 129.8, 114.7, 79.9, 74.3, 69.4, 67.9, 58.0, 26.0, 25.8.

Synthesis of N-methoxy-N-methyl-2-(4-(4-(prop-2-ynyloxy)butoxy)phenyl)-1H-benzo[d]imidazole-6-carboxamide (DPA 154-b)

To % solution of N-Methoxy, N-methyl 3, 4 dinitrobenzamide (0.73 g, 2.86 mmol) in ethanol-ethyl acetate mixture (40.0 mL, 3:1 v/v), 10% Pd—C (0.30 g) was added. Hydrogenation at the atmospheric pressure for 5 hours yielded corresponding diamine which was used without further characterization after filtration of the catalyst ($R_f$=0.46 in dichloromethane:methanol 9:1, v/v). 4-(4-(prop-2-ynyloxy) butoxy)benzaldehyde (0.70 g, 2.86 mmol) and sodium metabisulfite (0.54 g, 2.86 mmol) in water (1.00 mL) were added into it and the reaction mixture was refluxed for 6 hours. Volatiles were evaporated under reduced pressure. The crude product was purified by column chromatography on a silica gel using dichloromethane-methanol as eluent to afford the desired product as pale yellow gummy solid (0.70 g, 61%): $R_f$=0.50 (in dichloromethane-methanol 9:1 v/v); IR (neat, cm$^{-1}$) 3231 (alkyne C—H stretch), 2230 (alkyne C—C stretch), 1608; $^1$H NMR (500 MHz, methanol-$d_4$) δ 7.98 (dd, $J_1$=8.90 Hz, $J_2$=2.00 Hz, 2H), 7.93 (br, 1H), 7.59-7.55 (m, 2H), 6.99 (dd, $J_1$=8.65, $J_2$=2.00, 2H), 4.13 (d, J=2.39 Hz, 2H, —CH$_2$OCH$_2$CCH), 3.97 (t, J=6.27 Hz, 2H, —OCH$_2$CH$_2$—), 3.61 (s, 3H), 3.55 (t, J=6.40 Hz, 2H), 3.39 (s, 3H), 2.85 (t, J=2.26 Hz, 1H, —CH$_2$OCH$_2$CCH), 1.84-1.78 (m, 2H), 1.74-1.68 (m, 2H) (Imino proton was not observed because of exchange with the NMR solvent); $^{13}$C NMR (75 MHz, methanol-$d_4$) δ 170.5, 161.1, 154.1, 140.5, 138.4, 128.1, 127.6, 122.7, 121.2, 114.6, 113.6, 79.5, 74.3, 69.4, 69.1, 67.5, 60.1, 57.3, 33.4, 25.74, 25.70; MS (MALDI-TOF) m/z calcd for $C_{23}H_{25}N_3O_4$ [M]$^+$, 407.18. found 407.10 ([M]$^+$).

Synthesis of 2-(4-(4-(prop-2-ynyloxy)butoxy)phenyl)-1H-benzo[d]imidazole-6-carbaldehyde (DPA 154-c)

To a solution of N-methoxy-N-methyl-2-(4-(4-(prop-2-ynyloxy)butoxy)phenyl)-1H-benzo[d]imidazole-6-carboxamide (0.70 g, 1.71 mmol) in THF-ether (80.0 mL, 3:1), lithium aluminum hydride (0.26 g, 6.58 mmol) was added at −78° C. and then allowed to warm up and stirred at 0° C. for 6 hours. The reaction mixture was quenched by the addition of saturated ammonium chloride solution (100 mL). The grey solid that precipitated out was filtered off. The filtrate was extracted with ethyl acetate (3×75 mL). Organic layers were combined and dried over sodium sulfate. Volatiles were removed under reduced pressure. The crude product was purified by column chromatography on silica gel using hexanes-ethyl acetate (0-80% ethyl acetate in hexanes) as eluent to yield the desired compound as a light yellow liquid (0.33 g, 55%); $R_f$=0.65 (ethyl acetate-hexane 8:2 v/v); IR (neat, cm$^{-1}$) 2945 (aromatic C—H stretch), 2066 (alkyne C—C stretch), 1686; $^1$H NMR (500 MHz, methanol-$d_4$) δ 9.99 (s, 1H), 8.08 (s, br, 1H), 8.00 (dd, $J_1$=8.82 Hz, $J_2$=1.95 Hz, 2H), 7.80 (dd, $J_1$=8.28 Hz, $J_2$=1.46 Hz, 1H), 7.67 (s, br, 1H), 7.05 (dd, $J_1$=9.06 Hz, $J_2$=2.01 Hz, 2H), 4.18 (d, J=2.32 Hz, 2H, —CH$_2$OCH$_2$CCH), 4.05 (t, J=6.32 Hz, 2H, —OCH$_2$CH$_2$—), 3.61 (t, J=6.27 Hz, 2H), 2.87 (t, J=2.56 Hz, 1H, —CH$_2$OCH$_2$CCH), 1.91-1.85 (m, 2H), 1.80-1.75 (m, 2H) (Imino proton was not observed because of exchange with the NMR solvent); $^{13}$C NMR (75 MHz, methanol-$d_4$) δ 192.4, 161.4, 131.7, 128.3, 123.7, 120.0, 114.7, 79.4, 74.2, 69.1, 67.5, 57.3, 29.13, 25.73, 25.70 (Four aromatic carbon peaks were not observed likely because of aggregation of the molecule); MS (MALDI-TOF) m/z for $C_{21}H_{20}N_2O_3$[M]$^+$ calcd 348.15. found 349.48 [M+H]$^+$.

Synthesis of 6-(4-methylpiperazin-1-yl)-2'-(4-(4-(prop-2-ynyloxy)butoxy)phenyl)-1H,3'H-2,5'-bibenzo[d]imidazole (DPA 154)

To a solution of 5-(4-methylpiperazin-1-yl)-2-nitroaniline (0.21 g, 0.91 mmol) in ethanol-ethyl acetate mixture (20.0 mL), Pd—C (0.15 g) was added and the mixture was hydrogenated for 5 hours at the atmospheric pressure. Charcoal was filtered off. To this solution, 2-(4-(4-(prop-2-ynyloxy)butoxy)phenyl)-1H-benzo[d]imidazole-6-carbaldehyde (0.32 g, 0.91 mmol) and a solution of $Na_2S_2O_5$ (0.17 g, 0.91 mmol) in water (1.00 mL) were added. The mixture was refluxed for 12 hours following which it was allowed to come to room temperature. Volatiles were removed under reduced pressure. The crude mixture was purified by column chromatography on a silica gel column using dichloromethane-methanol as eluent (0-15% methanol in dichloromethane) which afforded the desired product as yellow solid (0.29 g, 60%): $R_f$=0.40 (dichloromethane-methanol 8:2 v/v); mp 150-155° C.; IR (neat, cm$^{-1}$) 2236 (alkyne C—C stretch), 1630, 1433; $^1$H NMR (300 MHz, methanol-$d_4$) δ 8.21 (d, J=1.11 Hz, 1H) 7.98 (dd, $J_1$=8.86 Hz, $J_2$=2.00 Hz, 2H), 7.91 (dd, $J_1$=8.46 Hz, $J_2$=1.75 Hz, 1H), 7.65 (d, J=8.46 Hz, 1H), 7.50 (d, J=8.86 Hz, 1H), 7.14 (d, J=2.00 Hz, 1H), 7.04-7.00 (m, 3H), 4.17 (d, J=2.47 Hz, 2H), 4.01 (t, J=6.15 Hz, 2H), 3.59 (t, J=6.14 Hz, 2H), 3.34-3.30 (Some peaks are masked with the NMR solvent signal) 3.03 (t, J=4.63 Hz, 4H), 2.86 (t, J=2.32 Hz, 1H), 2.66 (s, 3H), 1.88-1.72 (m, 4H) (Imino protons were not observed because of exchange with the NMR solvent); $^{13}$C NMR (75 MHz, methanol-$d_4$) δ 161.1, 153.9, 152.4, 147.4, 138.9, 134.5, 129.9, 128.1 (two peaks), 124.2, 121.3, 121.0, 115.1, 115.0, 114.5, 112.1, 101.3, 79.4, 74.2, 71.2, 69.1, 67.5, 63.5, 57.3, 54.2, 49.3, 43.5, 25.7; ESI-HRMS (m/z) m/z calcd. for $C_{32}H_{35}N_6O_2$ 535.2821. found 535.2814; HPLC: $t_R$ 2.46 min, purity 98.6% (see procedure for method details).

HPLC Analysis:

HPLC analysis of compounds DPA 151-154 was performed on HP1100 series analytical HPLC instrument. The experiments were performed on a Supelcosil LC-18S column using the following gradient conditions.

DPA 151: 40% B in A with initial hold for 2 minutes and then equilibrate at 40% B in A to 100% B over 8 minutes at a flow rate of 2.0 mL/minute; DPA 152: 60% B in A with initial hold for 2 minutes and then equilibrate at 60% B in A to 100% B over 8 minutes at a flow rate of 2.0 mL/minute; DPA 153: 60% B in A with initial hold for 2 minutes and then equilibrate at 60% B in A to 100% B over 8 minutes. This was followed by 100% B over next five minutes at a flow rate of 2.0 mL/minute; DPA 154: 60% B in A with initial hold for 2 minutes and then equilibrate at 60% B in A to 100% B over 8 minutes. This was followed by 100% B over next five minutes at a flow rate of 2.0 mL/minute. Where, A—H$_2$O containing 0.1% trifluoroacetic acid and B— 95:5 CH$_3$CN—H$_2$O Nucleic Acids:

Nucleic acids were purchased from Integrated DNA Technologies (Coraville, Iowa). The concentration of the nucleic acid was determined using the extinction coefficient provided by the supplier. The DNA duplex was prepared by heating the dA$_{60}$ and dT$_{60}$ in equimolar ratio in buffer 10 mM sodium cacodylate, 0.1 mM EDTA and 100 mM NaCl at pH 7.0 at 95° C. for 15 minutes and then slowly allowing it to cool back to room temperature. After two days of incubation, the duplex formation was checked by UV thermal denaturation experiments. The stock solution was stored at 4° C. and diluted to desired concentrations as required.

Ultra Violet (UV) Thermal Denaturation Experiments:

All UV spectra were obtained on a 12 cell holder Cary 1E UV-Vis spectrophotometer equipped with temperature controller. Quartz cells with 1 cm path length were used for all the experiments. Spectrophotometer stability and wavelength alignment were checked prior to initiation of each thermal denaturation experiment. For all experiments, the samples were prepared by diluting a stock sample. The melting of DNA with and without the ligand was performed at a heating rate of 0.2° C./min. Samples were brought back to 20° C. after the experiment. All UV melting experiments were monitored at 260 nm. For the $T_m$ determinations, derivatives were used. Data points were recorded every 1.0° C. The DNA concentration was 1 µM/duplex while the ligand concentration was 10 µM. All ligand solutions were prepared in dimethyl sulfoxide (DMSO) as concentrated stock solution (6-10 mM) and diluted to desired concentrations in buffer.

Minimum Inhibitory Concentration (MIC) Determination:

Bacteria used in this study were *Staphylococcus aureus* ATCC 29213, *Escherichia coli* ATCC 25922, *Escherichia coli* K12, *Staphylococcus aureus* ATCC 33591, *Pseudomonas aeruginosa* ATCC 27853, and *Enterococcus faecalis* ATCC 29212. All compounds were tested by the microbroth dilution method following Clinical and Laboratory Standards Institute guidelines. Briefly, Mueller-Hinton broth (Difco Laboratories, Becton Dickinson) was inoculated with each organism and incubated at 37° C. with shaking to establish logarithmic growth. Following incubation, each culture was pelleted by centrifugation (3,500×g for 5 min) and resuspended in 0.85% sterile saline solution to an optical density at 625 nm of 0.1. Samples were tested in triplicate using 96 well microplates (Corning Costar Corp. Cambridge, Mass.), yielding final bacterial concentrations of $5\times10^5$ CFU/mL, and incubated for 24 h at 37° C. Following incubation, optical densities of each well were determined with a µQuant microplate spectrophotometer (BioTek Instruments, Inc., Winooski, Vt.) at 625 nm. The MIC was defined as the lowest concentration needed to completely inhibit growth as compared to no treatment controls.

Inhibition Assays Against *E. coli* DNA Topoisomerase I:

Inhibition assays were used to determine the activities of the newly synthesized compounds against *E. coli* DNA topoisomerase I. The reaction mixture (30 µl) contained 20 mM Tris-HCl at pH 7.9, 50 mM KAc, 10 mM $Mg(Ac)_2$, 1 mM DTT, 1 µg/mL BSA, 150 ng of the supercoiled plasmid pBAD-GFPuv, 6 nM of *E. coli* topoisomerase I, and one of the compounds at a specified concentration that ranges from 0.5 to 45 µM. All components were assembled on ice and incubated for 15 min at 37° C. After the incubation, the reactions were terminated by extraction with an equal volume of phenol. The topological state of the DNA samples was analyzed with 1% agarose gel electrophoresis in 1×TAE buffer, pH 7.8. Following electrophoresis, the agarose gel was stained with Ethidium Bromide, destained, and photographed under UV light. The intensity of DNA topoisomers was determined using KODAK 1D Image Analysis Software. The percentage of (−) supercoiled DNA was calculated from a comparison of the intensity of the (−) supercoiled band with the total intensity of all DNA topoisomers. The $IC_{50}$ was calculated as the amount of the drug for which 50% of the DNA was still in a (−) supercoiled state.

Inhibition Assays Against *E. coli* DNA Gyrase:

The reaction mixture (30 µl) contained 35 mM Tris-HCl at pH 7.5, 24 mM KCl, 4 mM $MgCl_2$, 2 mM DTT, 1.75 mM ATP, 5 mM spermidine, 0.1 mg/ml BSA, 6.5% glycerol, 250 ng of the relaxed plasmid pBAD-GFPuv, 0.5 units of *E. coli* DNA Gyrase, and one of the compounds at a final concentration that ranges from 1 to 50 µM. All components were assembled on ice and incubated for 30 minutes at 37° C. After the incubation, the reactions were terminated by extraction with an equal volume of phenol. The topological state of the DNA samples was analyzed with 1% agarose gel electrophoresis in 1×TAE buffer, pH 7.8. Following electrophoresis, the agarose gel was stained with Ethidium Bromide, destained, and photographed under UV light. The intensity of DNA topoisomers was determined using KODAK 1D Image Analysis Software.

Inhibition Assays Against Human DNA Topoisomerase I:

The inhibition assays were used to determine the activities of the newly synthesized compounds against Human DNA topoisomerase I. The reaction mixture (25 µl) contained 20 mM Tris-HCl at pH 7.9, 50 mM KAc, 10 mM $Mg(Ac)_2$, 1 mM DTT, 1 µg/ml BSA, 250 ng of the supercoiled plasmid pBAD-GFPuv, 2 units of Human DNA topoisomerase I, and one of the compounds at a final concentration that ranges from 5 to 50 µM. All components were assembled on ice and incubated for 30 minutes at 37° C. After the incubation, the reactions were terminated by extraction with an equal volume of phenol. The topological state of the DNA samples was analyzed with 1% agarose gel electrophoresis in 1×TAE buffer, pH 7.8. Following electrophoresis, the agarose gel was stained with Ethidium Bromide, destained, and photographed under UV light. The intensity of DNA topoisomers was determined using KODAK 1D Image Analysis Software. The percentage of (−) supercoiled DNA was calculated from a comparison of the intensity of the (−) supercoiled band with the total intensity of all DNA topoisomers. The $IC_{50}$ was calculated as the amount of the drug for which 50% of the DNA was in a (−) supercoiled state.

Inhibition Assays Against Human DNA Topoisomerase II:

The reaction mixture (25 µl) contained 20 mM Tris-HCl at pH 7.9, 50 mM KAc, 10 mM $Mg(Ac)_2$, 1 mM DTT, 1 µg/mL BSA, 200 ng supercoiled plasmid pBAD-GFPuv, 4 units of Human topoisomerase II, and one of the compounds at a final concentration that ranges from 5 to 50 µM. All components were assembled on ice and incubated for 30 minutes at 37° C. After the incubation, the reactions were terminated by extraction with an equal volume of phenol. The topological state of the DNA samples was analyzed with 1% agarose gel electrophoresis in 1×TAE buffer, pH 7.8. Following electrophoresis, the agarose gel was stained with Ethidium Bromide, destained, and photographed under UV light. The intensity of DNA topoisomers was determined using KODAK 1D Image Analysis Software. The percentage of (−) supercoiled DNA was calculated from a comparison of the intensity of the (−) supercoiled band with the total intensity of all DNA topoisomers. The $IC_{50}$ was calculated as the amount of the drug for which 50% of the DNA was in a (−) supercoiled state.

Cytotoxicity Experiments:

The DU 145 cell line was cultured according to ATCC protocols. Cells were harvested using trypsin-EDTA solution and counted using trypan blue exclusion. Cells were seeded at a volume of 100 µl/well in the wells of tissue culture treated 96 well plates at a density of $10\times10^5$ cells per well. Seeded 96 well plates were returned to incubator (37° C., 5% $CO_2$) for twenty-four hours to resume exponential growth.

Test compounds (Hoechst 33258, Hoechst 33342, DPA 151, DPA 152, DPA 153 and DPA 154) and known drug control (cisplatin) were diluted in appropriate culture media to the following concentrations: 40, 20, 10, 5, 2.5, 1.25 and 0.125 µM. Cell lines were then treated with 100 µl of each test compound or cisplatin in triplicate. The final concentrations of each treatment were: 20, 10, 5, 2.5, 1.25, 0.625 and 0.0625 µM. Each plate also contained wells containing untreated cells and media only as controls. After receiving treatments, the 96 well plates were returned to incubator (37° C., 5% $CO_2$) for forty-eight hours.

After forty-eight hours of treatment, the treated plates were fixed with trichloroacetic acid and stained with sulforhodamine B using a modified version of the protocol described by Skehan et al. In short, 50 μl of cold 80% TCA was added to each well, at a final concentration of 16% TCA, and plates were incubated at 4° C. for one hour. The media and TCA solution was discarded and plates were washed four times using room temperature tap water. Plates were allowed to air dry overnight. Plates were stained with the addition of 70 μl/well of 40% (w/v) SRB in 1% (v/v) acetic acid solution. Samples were stained for fifteen minutes and then stain was discarded. Plates were then washed four times with 1% (v/v) acetic acid solution to remove unbound stain and allowed to air dry overnight at room temperature. Finally, SRB stain was solubilized by adding 150 μl of 10 mM unbuffered Tris base to each well. The absorbance of each samples at 560 nm was recorded using a Tecan plate reader and the $IC_{50}$ was determined using Origin 4.0 software. Each study was completed in duplicate.

Example 1—Synthesis of Ligands DPA 151-154

The synthesis of the ligands (DPA 151-154) was performed using a divergent strategy (Ji, Y. et al., *Med. Chem.* (2001) 9, 2905-2919; Tanada, M. et al., *J. Org. Chem.* (2006) 71, 125-134) to construct the alkyl linkers (see FIG. 2). To introduce the linkers, Mitsunobu reactions were carried out of 4-hydroxy benzaldehyde with aliphatic alcohols (1-4) that terminated in the requisite alkyne functionality. The aliphatic alcohols were obtained commercially or prepared in one step from a corresponding diol. The 4-substituted benzaldehydes (DPA 151a-DPA 154a) were coupled with 3, 4-diamino-N-methoxy-N-methylbenzamide in the presence of an oxidant to yield the corresponding benzimidazoles (DPA 151b-DPA 154b). These benzimidazoles containing the weinreb amide functionality were then easily reduced to their corresponding aldehydes (DPA 151c-DPA 154c) using lithium aluminum hydride. Coupling of these aldehydes with 4-(4-methylpiperazin-1-yl) benzene-1, 2-diamine, (Kelly, D. P. et al., *Aust. J. Chem.* (1994) 47, 247-262) in the presence of an oxidant resulted in the synthesis of target bisbenzimidazoles DPA 151-DPA 154 in good yields. The presence of a rather inert functional group alkyne also makes these molecules useful for further modifications using click chemistry applications. All compounds were characterized by spectroscopic techniques (NMR, IR and HRMS/MALDI-TOF).

Example 2—Inhibition of Bacterial DNA Topoisomerase I

The inhibitory activities of the newly synthesized bisbenzimidazoles were tested against a few DNA topoisomerases, i.e., *E. coli* DNA topoisomerase I, *E. coli* DNA gyrase, human DNA topoisomerase I, and human DNA topoisomerase II.

These newly synthesized compounds showed a selective and enhanced inhibition against *E. coli* DNA topoisomerase I.

Figure 6:
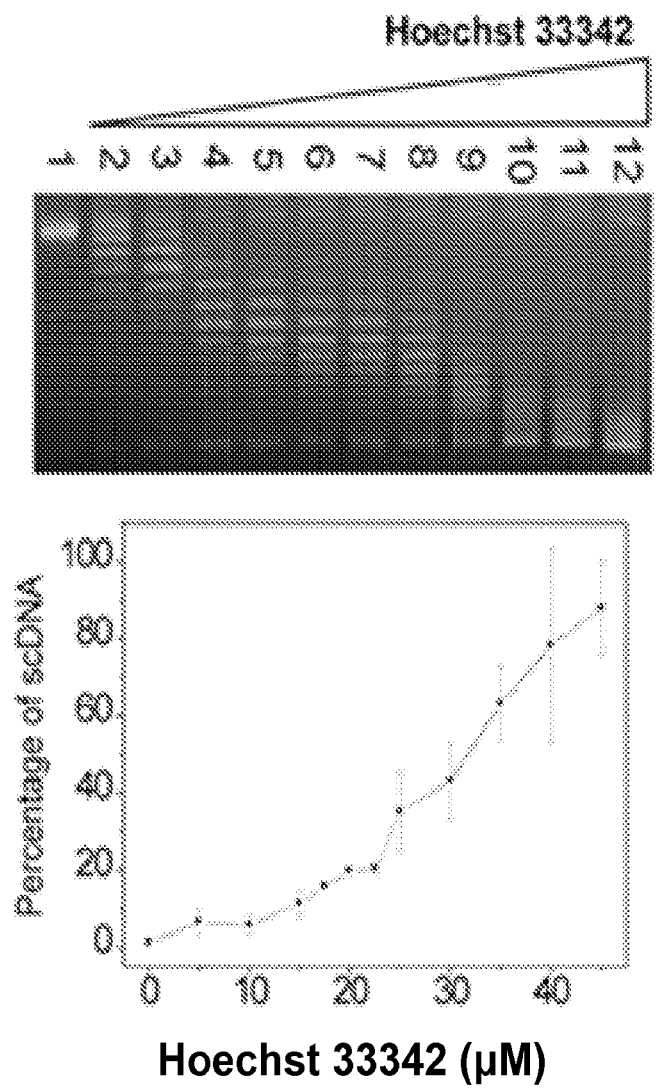
FIG. 6 shows the inhibitory activities of compound Hoechst 33342 against *E. coli* DNA topoisomerase I. The *E. coli* DNA topoisomerase I inhibition assays were performed as described in Materials and Methods. The plasmid DNA molecules were isolated and subjected to 1% agarose gel electrophoresis in the absence of chloroquine. Lanes 1 to 12 contain 0, 5.0, 10.0, 15.0, 17.5, 20.0, 22.5, 25.0, 30.0, 35.0, 40.0, and 45.0 μM of Hoechst 33342, respectively. The bottom panel shows the quantification analysis of the inhibitory activities of Hoechst 33342.

FIGS. 3A-3C show the results of inhibitory assays of Hoechst 33258 and its derivative, DPA151, against *E. coli* DNA topoisomerase I. In the absence of Hoechst 33258 or DPA151, 6 nM of *E. coli* DNA topoismerase I was sufficient to relax the supercoiled plasmid DNA template, pBAD-GFPuv (lanes 1 of FIGS. 3A and 3B). The titration of increasing amounts of either compound into the reaction mixtures resulted in the inhibition of *E. coli* DNA topoisomerase I. For Hoechst 33258, approximately 20 μM was needed to completely inhibit the activities of *E. coli* DNA topoisomerase I (lane 10 of FIG. 3A). In contrast, it took only approximately 5 μM of DPA151 to fully suppress the activities of *E. coli* DNA topoisomerase I (lane 9 of FIG. 3B). The $IC_{50}$ of Hoechst 33258 and DPA151 were determined to be 19.50±1.32 and 5.50±0.50 μM, respectively (FIG. 3C and Table 1). These results demonstrated that the addition of a hydrophobic group to the hydroxyl tail of Hoechst 33258 dramatically increased the inhibitory capacity against *E. coli* DNA topoisomerase I. Similar results were also obtained for DPA152, 153 and 154 in which hydrophobic groups with different lengths were added to the hydroxyl group of Hoechst 33258. These results are summarized in Table 1 and FIGS. 4A-4B to FIG. 6.

TABLE 1

$IC_{50}$ values of the newly synthesized bisbenzimidazoles against *E. coli* DNA topoisomerase I, human DNA topoisomerase I, and human DNA topoisomerase II

| Compound | $IC_{50}$ (μM)[a] | | |
|---|---|---|---|
| | ecTopo I[b] | hTopo I[b] | hTopo II[b] |
| Hoechst 33258 | 19.50 ± 1.32 | 22.86 ± 1.55 | 28.92 ± 4.45 |
| Hoechst 33342 | 29.83 ± 2.75 | >50 μM | — |
| DPA151 | 5.50 ± 0.50 | 25.41 ± 2.20 | 51.6 ± 2.5 |
| DPA152 | 4.57 ± 0.81 | >50 μM | — |
| DPA153 | 2.47 ± 0.06 | >50 μM | — |
| DPA154 | 6.63 ± 0.47 | >50 μM | — |

[a]$IC_{50}$ was determined as described under the materials and methods section. The values are the average of at least three independent determinations.
[b]ecTopo I, hTopo I, and hTopo II represent *E. coli* DNA topoisomerase I, human DNA topoisomerase I, and human DNA topoisomerase II, respectively.

Example 3—Inhibition of Human DNA Topoisomerase I

Figure 7:
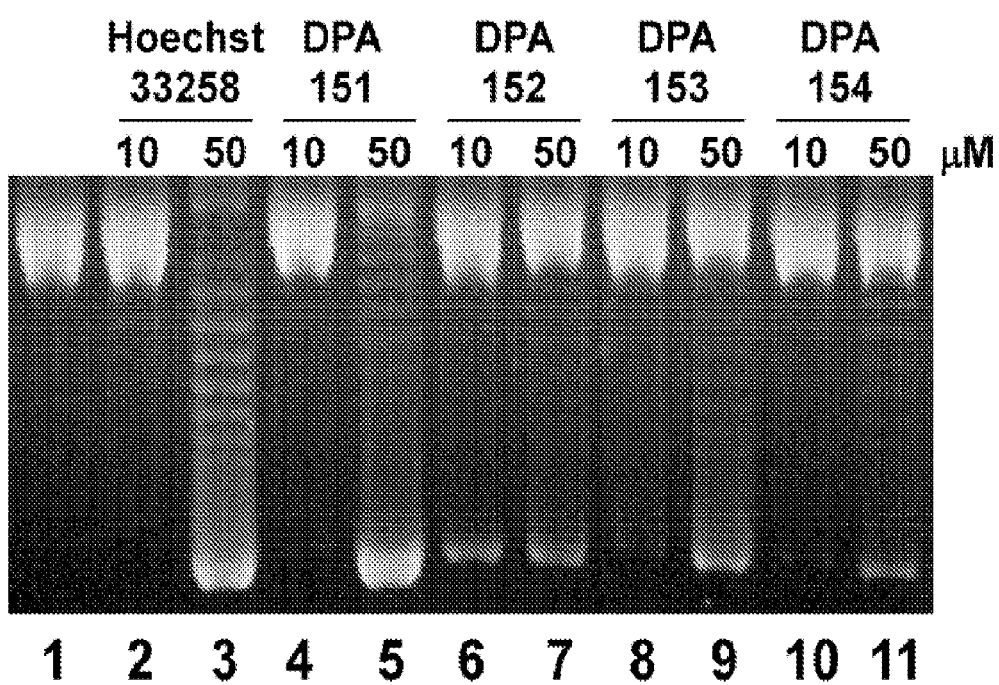
FIG. 7 shows decreased inhibitions of the newly synthesized bisbenzimidazoles against human DNA topoisomerase I. Inhibition assays against human topoisomerase I were performed as described in Materials and Methods in the presence of one of the bisbenzimidazoles. Following the inhibition assays, the plasmid DNA molecules were isolated and subjected to 1% agarose gel electrophoresis in the absence of chloroquine. Lane 1 represents the relaxed plasmid DNA pBAD-GFPuv. Two different concentrations for each compound (10 and 50 μM) were used in these assays.

Next, the inhibitory activities of these newly synthesized bisbenzimidazoles against human DNA topoisomerase I, a type IB topoisomerase, was examined FIG. 7 shows the results.

Figure 8A:
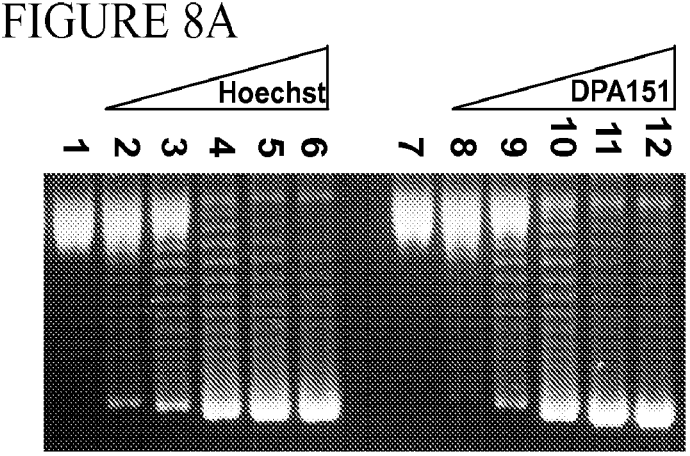
FIGS. 8A-8B show the inhibitory activities of compounds Hoechst 33258 and DPA151 against human DNA topoisomerase I. The human DNA topoisomerase I inhibition assays were performed as described in Materials and Methods. The plasmid DNA molecules were isolated and subjected to 1% agarose gel electrophoresis in the absence of chloroquine. (A) Lanes 1 to 6 contain 0, 5.0, 10.0, 25.0, 40.0, and 50.0 µM of Hoechst 33258. Lanes 7 to 12 contain 0, 5.0, 10.0, 25.0, 40.0, and 50.0 µM of compound DPA151, respectively. (B) Quantification analysis of the inhibitory activities of Hoechst 33258 (close square) and DPA151 (close circle) against human topoisomerase I.
Figure 8B:
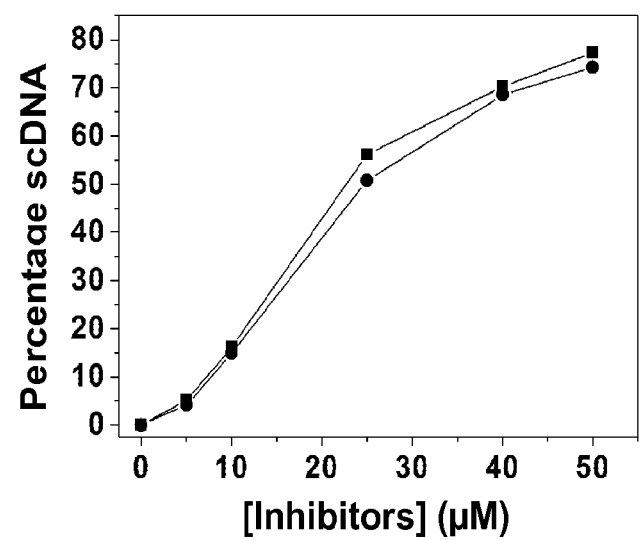

For Hoechst 33258 and DPA151, 50 μM of these two compounds was able to prevent about 70% (FIG. 8B) of supercoiled DNA template from relaxation by human DNA topoisomerase I (compare lanes 3 and 5 to lane 1 of FIG. 7). However, 50 μM of other newly synthesized bisbenzimidazoles was only capable of preventing 5-15% of supercoiled DNA from relaxation (FIG. 7).

These results suggest that the addition of a hydrophobic tail to the hydroxyl group of Hoechst 33258 significantly reduced the inhibitory activities against human DNA topoisomerase I.

Figure 9A:
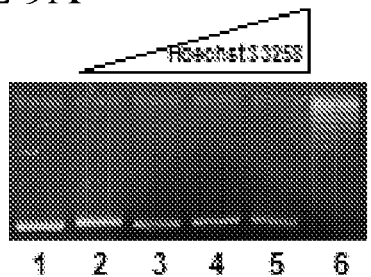
FIGS. 9A-9C show the inhibitory activities of compounds (A) Hoechst 33258, (B) DPA151, DPA152, DPA153 and (C) DPA154, DPA157 against E. coli DNA Gyrase. The E. coli DNA Gyrase inhibition assays were performed as described in Materials and Methods. The plasmid DNA molecules were isolated and subjected to 1% agarose gel electrophoresis in the absence of chloroquine. (A) Lanes 1 and 6 are the supercoiled and relaxed plasmid DNA pBAD-GFPuv, respectively. Lanes 2 to 5 contain 0, 1.0, 10.0, and 50.0 µM of Hoechst 33258, respectively. (B) Lanes 1 and 11 are the supercoiled and relaxed plasmid DNA pBAD-GFPuv, respectively. Lanes 2 to 4 contain 0, 1.0, and 10.0 µM of DPA151, respectively. Lanes 5 to 7 contain 1.0, 10.0, and 50.0 µM of DPA152, respectively. Lanes 8 to 10 contain 1.0, 10.0, and 50.0 µM of DPA153, respectively. (C) Lanes 1 and 9 are the supercoiled and relaxed plasmid DNA pBAD-GFPuv, respectively. Lanes 2 to 5 contain 0.0, 1.0, 10.0, and 50.0 µM of DPA154, respectively.
Figure 9B:
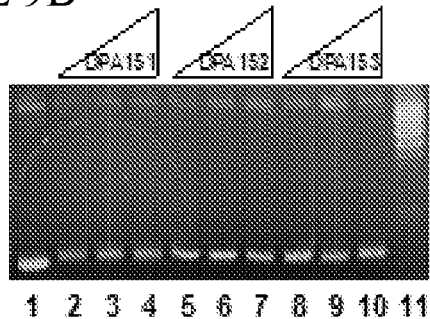
Figure 9C:
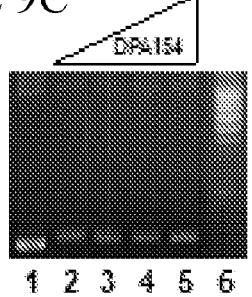
Figure 10:
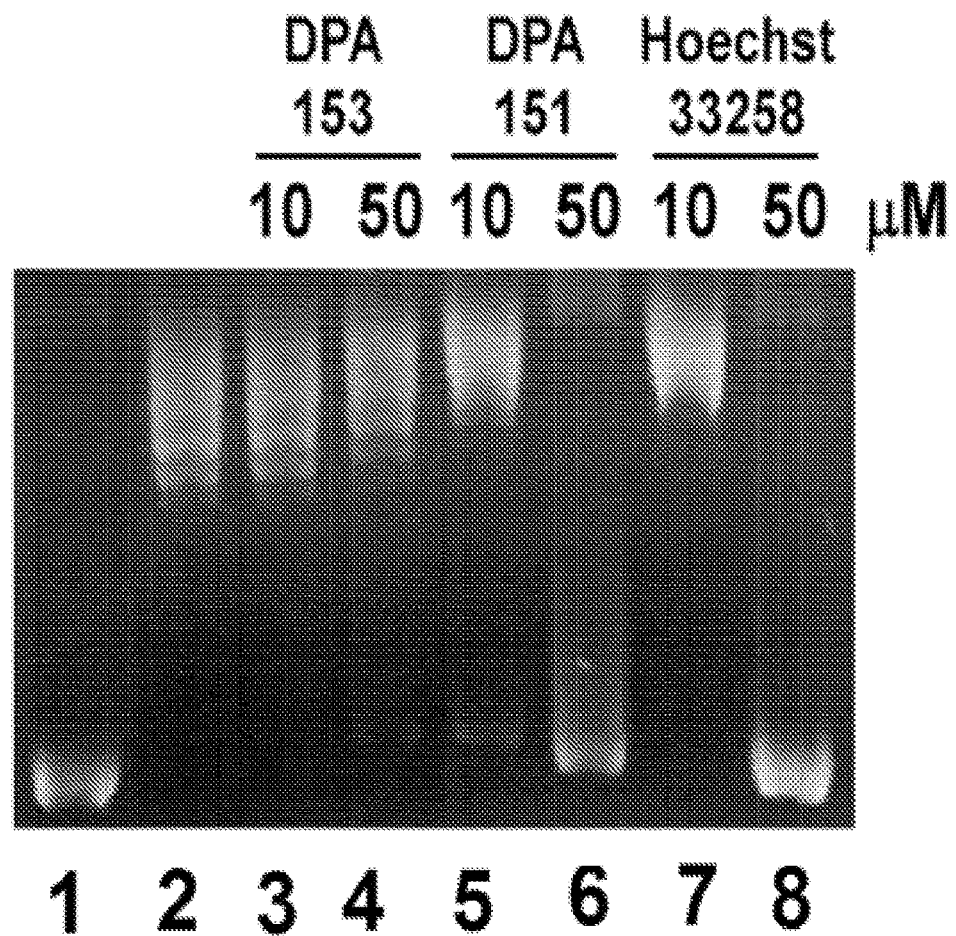
FIG. 10 shows inhibitory activities of DPA151, DPA153, and Hoechst 33258 against human DNA topoisomerase II. Inhibition Assays against human DNA topoisomerase II were performed as described in the Materials and Methods section. The plasmid DNA molecules were isolated and subjected to 1% agarose gel electrophoresis in the absence of chloroquine. Lanes 1 and 2 are the supercoiled and relaxed plasmid DNA template pBAD-GFPuv, respectively. Two different concentrations for each compound (10 and 50 µM) were used in these assays.
Figure 11A:
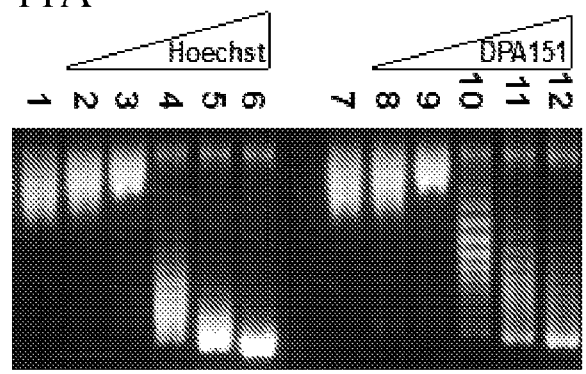
FIGS. 11A-11B show the inhibitory activities of compounds Hoechst 33258 and DPA151 against human DNA topoisomerase II. The human DNA topoisomerase II inhibition assays were performed as described in Materials and Methods. The plasmid DNA molecules were isolated and subjected to 1% agarose gel electrophoresis in the absence of chloroquine. (A) Lanes 1 to 6 contain 0, 5.0, 10.0, 25.0, 40.0, and 50.0 µM of Hoechst 33258, respectively. Lanes 7 to 12 contain 0, 5.0, 10.0, 25.0, 40.0, and 50.0 µM of DPA151, respectively. (B) Quantification analysis of the inhibitory activities of Hoechst 33258 (close squares) and DPA151 (close circles) against human topoisomerase II.
Figure 11B:
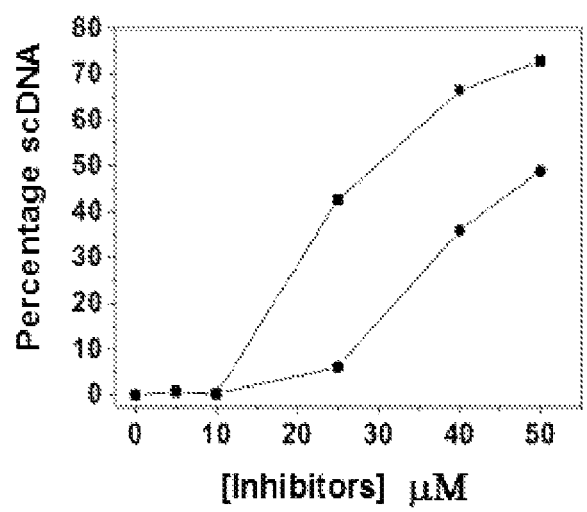
Figure 12A:
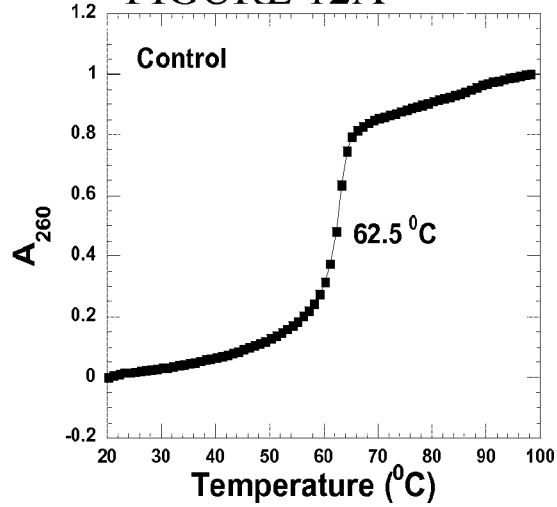
FIGS. 12A-12E show the UV thermal denaturation profiles of all ligands studied with $dA_{60}.dT_{60}$ duplex. The DNA duplex (1 µM/duplex) was mixed with various ligands (as indicated on each graph) at 10 µM concentration and denatured in the temperature range 20° C.-98° C. at a rate of 0.2° C./min in buffer 10 mM sodium cacodylate, 0.1 mM EDTA and 100 mM NaCl at pH 7.0.
Figure 12B:
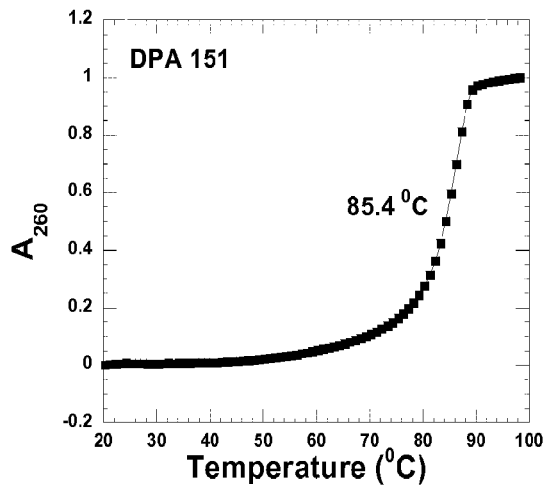
Figure 12C:
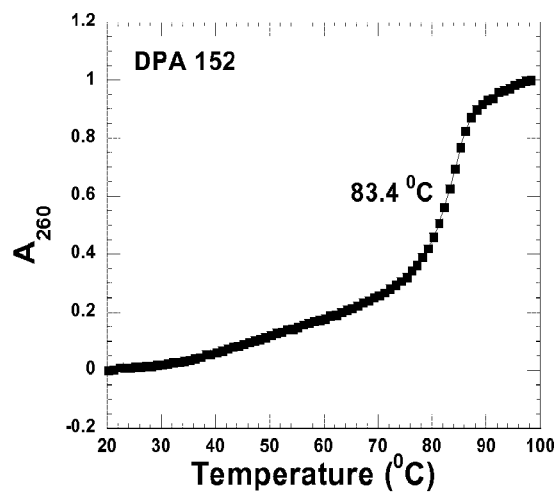
Figure 12D:
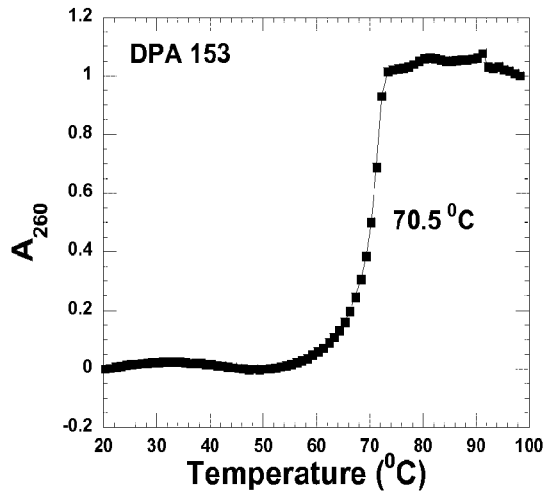
Figure 12E:
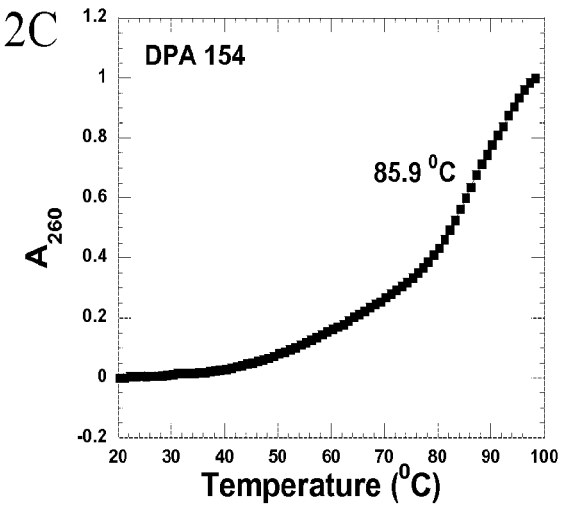

In this study, the inhibitory activities of these newly synthesized compounds against two type II topoisomerases, *E. coli* DNA gyrase and human DNA topoisomerase II, were also tested. The results showed that Hoechst 33258 and the newly synthesized bisbenzimidazoles did not inhibit DNA gyrase's activities under our experimental conditions (FIGS. 9A-9C). For human DNA topoisomerase II, 50 μM of Hoechst 33258 was sufficient to completely inhibit its activities (lane 10 of FIG. 3A). In contrast, the addition of a hydrophobic moiety to the hydroxyl group of Hoechst 33258 completely eliminated the inhibition of 50 μM of these newly synthesized compounds against human DNA topoisomerase II except DPA151 (FIG. 10; 50 μM of DPA151 partially inhibit the activities of human DNA topoisomerase II). The IC50 values of Hoechst 33258 and DPA151 against human topoisomerases I and II are summarized in Table 1 and FIGS. 11A-11B.

Example 4—UV Thermal Denaturation Studies

Bisbenzimidazoles are known to bind to the minor groove of AT rich DNA. The UV thermal denaturation experiments of the synthesized ligands were carried out with an AT rich DNA duplex. A 60 mer B-DNA duplex that was prepared by mixing equimolar amounts of a 60 mer homoadenine with a 60 mer homothymine polymer.

The results obtained from these experiments are shown in Table 2 and the denaturation curves in FIGS. 12A-12E.

The thermal denaturation experiments show some dependence of thermal stabilization on the length and composition of the linker present on the Hoechst 332258 derivatives DPA 151-DPA 154. As depicted in FIGS. 12A-12E, in the absence of ligand, the duplex dA60.dT60 exhibited a sharp hyperchroism at 62.5° C. indicating the dissociation of the duplex into single strands.

TABLE 2

A table showing the thermal denaturation temperatures of duplex DNA ($dA_{60}.dT_{60}$) in the presence of all studied ligands (10 μM each) in buffer 10 mM sodium cacodylate, 0.1 mM EDTA and 100 mM NaCl at pH 7.0.

| Ligand | Tm (° C.) | ΔTm (° C.) |
|---|---|---|
| None | 62.5 | — |
| Hoechst 33258 | 87.1 | 24.6 |
| Hoechst 33242 | 86.6 | 24.1 |
| DPA 151 | 85.4 | 22.9 |
| DPA 152 | 83.4 | 20.9 |
| DPA 153 | 70.5 | 8.0 |
| DPA 154 | 85.9 | 23.4 |

The thermal denaturation of dA60.dT60 was then carried out in the presence of DPA 151 (10 μM). At this concentration, the DNA was saturated with ligand, and lower concentrations (1-5 μM) of ligand resulted in biphasic thermal denaturation profiles. In the presence of DPA 151, a 22.9° C. thermal stabilization of DNA was observed. The thermal stabilization afforded by DPA 151 (22.9° C.) was similar to the thermal stabilization afforded by Hoechst 33258 and Hoechst 33242 (~24° C.). This thermal stabilization was, however, found to be dependent on the linker length and composition of the linker. As the linker length increases to a very long carbon chain (eleven atoms) in DPA 153, a significant drop in $\Delta T_m$ was observed (23.9° C. thermal stabilization for DPA 151 and 8° C. thermal stabilization for DPA 153). Control experiments with a GC rich calf thymus DNA showed very poor (1-2° C.) thermal stabilization of the DNA by DPA 151-154 that confirmed the preference of these ligands for AT rich DNA sequences. Surprisingly, DPA 153 is the most effective inhibitor of *E. coli* Topoisomerase I. The addition of a long hydrophobic linker, capable of aggregation, limits the DNA binding of the dye. However, in the presence of the topoisomerase, it is possible that DNA binding is restored as the hydrophobic pocket in the enzyme acts to free the ligand aggregation. An alternative explanation is that duplex DNA binding is not required for enzyme activity. The inhibitory activities of small molecules against these enzymes are believed to mainly stem from the binding of these ligands to the minor groove of the DNA double helix (Chen, A. Y. et al., *Cancer Research* (1993) 53, 1332-1337; Satz, A. L., et al., *Biochemistry* (2001) 40, 6465-6474). However, duplex DNA binding is not a sole criterion for effective topoisomerase inhibitions as a DNA non-binder, camptothecin, is a well-known DNA topoisomerase I poison (Wall, M. E., et al., *J. Am. Chem. Soc.* (1966) 88, 3888-3890; Hsiang, Y. H. et al., *Journal of Biological Chemistry* (1985) 260, 14873-14878). Cytotoxicity of these compounds against a prostate cancer cell line DU-145 was also tested. Considerable variation in toxicity was observed with changes in linker length. DPA 153, the most potent Topo I inhibitor, displayed much lower cytotoxicity ($IC_{50}$>10 μM) compared to Hoechst 33242 ($IC_{50}$=4.25 μM), whereas DPA 152 was nearly twice as toxic as Hoechst 33242. Table 3 shows $IC_{50}$ values of studies compounds against DU-145.

TABLE 3

$IC_{50}$ values of studies compounds against DU-145.

| Ligand | $IC_{50}$ (μM) |
|---|---|
| Hoechst 33242 | 4.25 ± 0.11 |
| DPA 151 | 3.24 ± 0.71 |
| DPA 152 | 2.12 ± 0.46 |
| DPA 153 | >10 |
| DPA 154 | 2.79 ± 0.13 |

Example 5—Antibacterial Activity

Compounds belonging to the bisbenzimidazole class of ligands have shown profound antibacterial effect against a variety of strains, which include methicillin-resistant *Staphylococcus aureus* (MRSA) and vancomycin-resistant *Enterococcus faecalis* (Hu, L. et al., *Bioorg. Med. Chem. Lett.* (2009) 19, 1292-1295; Hu, L. et al., *Bioorg. Med. Chem. Lett.* (2009) 19, 3374-3377). To discern if these inhibitors of *E. coli* Topoisomerase I are effective at inhibiting bacterial growth, the antibacterial effect of these compounds against both gram positive and gram negative strains was evaluated, as listed in Table 4.

In cases where a sharp inflection in the bacterial growth was not observed, the MIC is given as a range of values. As seen in Table 4, all four compounds are effective antibacterial compounds against a variety of strains, including the two *E. coli* strains. DPA 152 and DPA 154 show markedly improved activity against *E. faecalis* 29212. Both Hoechst dyes (33258 and 33242) are not good inhibitors of *E. faecalis* 29212. Of note also is that the molecular mass of DPA 151-154 is considerably higher than Hoechst 33342 (10-35% higher mass), implying that the antibacterial activities listed here (in μg/ml) are even better on a per mole basis for all newly synthesized compounds.

TABLE 4

Minimal inhibitory concentrations (MIC) of the studied ligands against various bacterial strains by microbroth dilution.

| Sample | MIC (μg/ml) | | | | | |
|---|---|---|---|---|---|---|
| | S1 | S2 | S3 | S4 | S5 | S6 |
| Ht 33258 | ≥32 | 16-32 | 16 | 16 | 16 | 16-32 |
| Ht 33342 | 2-4 | 2-4 | 8-16 | 16 | 8 | 16-32 |
| DPA 151 | 2-4 | 2-4 | 8 | 16 | 8 | 16-32 |
| DPA 152 | 2-4 | 2-4 | 8-16 | 16 | 8-16 | 4 |
| DPA 153 | 16 | 16 | 16 | 16 | 8-16 | 16-32 |
| DPA 154 | 2-4 | 2-4 | 8-16 | 16 | 8-16 | 8 |

S1 = *S. aureus* 29213;
S2 = *S. aureus* 33591;
S3 = *E. coli* 25922;
S4 = *P. aeruginosa* 27853;
S5 = *E. coli* K 12;
S6 = *E. faecalis* 29212

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those listed in the References section) are incorporated by reference in their entirety, including all figures and tables, to the extent they are not inconsistent with the explicit teachings of this specification.

REFERENCES

1. Y. Tse-Dinh *Infect. Disord.: Drug Targets* 2007, 7, 3-9.
2. Y. Tse-Dinh *Nucleic Acids Research* 2009, 37, 731-737.
3. J. J. Champoux *Annu. Rev. Biochem.* 200, 170, 369-413.
4. Y. Pommier *Chem. Rev.* 2009. 109, 2894-2902.
5. Y. H. Hsiang; R. Hertzberg; S. Hecht; L. F. Liu *Journal of Biological Chemistry* 1985, 260, 14873-14878.
6. C. Bailly Targeting DNA and topoisomerase I with indolocarbazole antitumor agents. In *Small Molecule DNA and RNA Binders;* 2003; Vol. 2; 2, pp 538-575.
7. C. Bailly *Curr. Med. Chem.* 20007, 39-58.
8. K. R. Hande *Eur. J. Cancer* 1998, 34, 1514-1521.
9. Z. Xu; T. K. Li; J. S. Kim; E. J. LaVoie; K. J. Breslauer; L. F. Liu; D. S. Pilch *Biochemistry* 1998, 37, 3558-3566.
10. S. J. Froelich-Ammon; N. Osheroff *J. Biol. Chem.* 1995, 270, 21429-32.
11. A. Y. Chen; C. Yu; B. Gatto; L. F. Liu *Proceedings of the National Academy of Sciences* 1993, 90, 8131-8135.
12. A. Y. Chen; C. Yu; A. Bodley; L. F. Peng; L. F. Liu *Cancer Research* 1993, 53, 1332-1337.
13. Z. Kazimierczuk; M. Andrzejewska; J. Kaustova; V. Klimesova *Eur. J. Med. Chem.* 2005, 40, 203-208.
14. G. R. Jadhav; M. U. Shaikh; R. P. Kale; M. R. Shiradkar; C. H. Gill *Eur. J. Med. Chem.* 2009, 44, 2930-2935.
15. S. Bansal; U. Tawar; M. Singh; A. Nikravesh; L. Good; V. Tandon *Int. J. Antimicrob. Agents* 2010, 35, 186-190.
16. B. Willis; D. P. Arya *Biochemistry* 2010, 49, 452-469.
17. B. Willis; D. P. Arya *Biochemistry* 2006, 45, 10217-10232.
18. B. J. Correa; D. Canzio; A. L. Kahane; P. M. Reddy; T. C. Bruice *Bioorg. Med. Chem. Lett.* 2006, 16, 3745-3750.
19. Y. Ji; D. Bur; W. Häsler; V. Runtz Schmitt; A. Dorn; C. Bailly; M. J. Waring; R. Hochstrasser; W. Leupin *Bioorg. Med. Chem.* 2001, 9, 2905-2919.
20. M. Tanada; S. Tsujita; S. Sasaki *J. Org. Chem.* 2006, 71, 125-134.
21. D. P. Kelly; S. A. Bateman; R. F. Martin; M. E. Reum; M. Rose; A. R. D. Whittaker *Aust. J. Chem.* 1994, 47, 247-262.
22. A. L. Satz; C. M. White; T. A. Beerman; T. C. Bruice *Biochemistry* 2001, 40, 6465-6474.
23. M. E. Wall; M. C. Wani; C. E. Cook; K. H. Palmer; A. T. McPhail; G. A. Sim *J. Am. Chem. Soc.* 1966, 88, 3888-3890.
24. L. Hu; M. L. Kully; D. W. Boykin; N. Abood *Bioorg. Med. Chem. Lett.* 2009, 19, 1292-1295.
25. L. Hu; M. L. Kully; D. W. Boykin; N. Abood *Bioorg. Med. Chem. Lett.* 2009, 19, 3374-3377.
26. S. Bansal; D. Sinha; M. Singh; B. Cheng; Y. Tse-Dinh; V. Tandon *Journal of Antimicrobial Chemotherapy* 2012, 67, 2882-2891.

We claim:

1. A compound of Formula I:

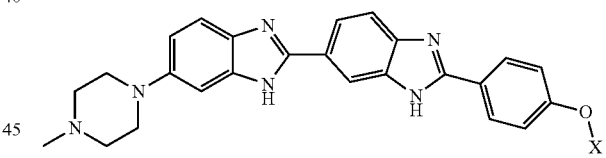

and salts thereof, wherein X is a terminal alkyne group having the structure C≡CH attached through a hydrophobic linker to the oxygen, wherein the hydrophobic linker is selected from $(CH_2)_9$ and $(CH_2)_4OCH_2$.

2. The compound, according to claim 1, which is 6-(4-methylpiperazin-1-yl)-2'-(4-(undec-10-ynyloxy) phenyl)-1H,3'H-2,5'-bibenzo[d]imidazole (termed DPA 153), which is represented by the Formula (Ic):

(Ic)

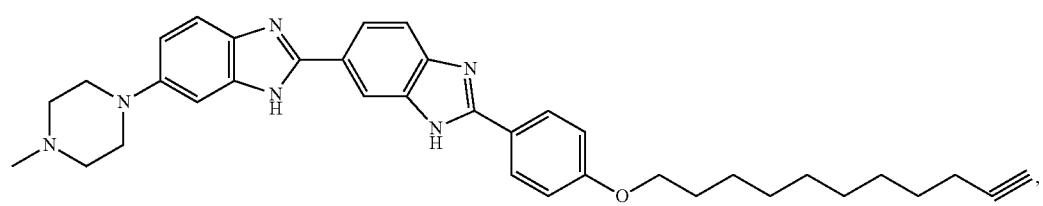

or a salt thereof.

3. A pharmaceutical composition comprising a compound of Formula I:

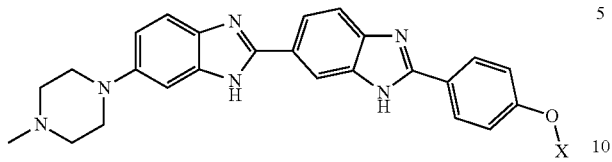

or a salt thereof, wherein X is a terminal alkyne group having the structure C≡CH, attached through a hydrophobic linker to the oxygen, wherein the hydrophobic linker is selected from $(CH_2)_9$ and $(CH_2)_4OCH_2$ and a pharmaceutically acceptable carrier or diluent.

4. The pharmaceutical composition, according to claim 3, further comprising one or more additional antibiotic compounds.

5. The pharmaceutical composition, according to claim 4, wherein the one or more additional antibiotic compounds are selected from beta-lactams, macrolides, tetracyclines, quinolones, aminoglycosides, sulfonamides, glycopeptides, and oxazolidinones.

6. A method for treating a bacterial infection, comprising administering, to a subject in need of such treatment, a compound of Formula I:

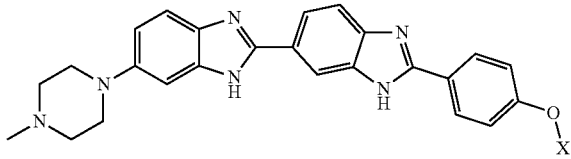

or a salt thereof, wherein X is a terminal alkyne group having the structure C≡CH attached through a hydrophobic linker to the oxygen, wherein the hydrophobic linker is selected from $CH_2$, $(CH_2)_4$, $(CH_2)_9$ and $(CH_2)_4OCH_2$.

7. A method of inhibiting topoisomerase I in bacteria, comprising administering, to the bacteria, a compound of Formula I:

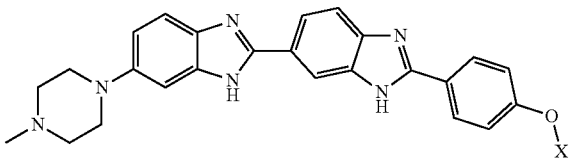

or a salt thereof, wherein X is a terminal alkyne group having the structure C≡CH attached through a hydrophobic linker to the oxygen, wherein the hydrophobic linker is selected from $CH_2$, $(CH_2)_4$, $(CH_2)_9$ and $(CH_2)_4OCH_2$.

8. A method for treating a bacterial infection, comprising administering, to a subject in need of such treatment, a compound selected from the group consisting of:

6-(4-methylpiperazin-1-yl)-2'-(4-(prop-2-ynyloxy)phenyl)-1H,3'H-2,5'-bibenzo[d]imidazole (termed DPA 151), which is represented by the Formula (Ia):

(Ia)

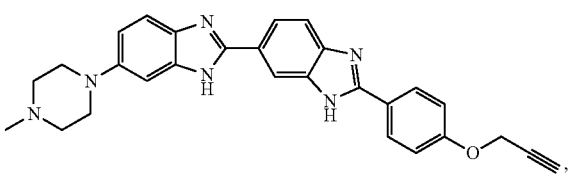

2'-(4-(hex-5-ynyloxy)phenyl)-6-(4-methylpiperazin-1-yl)-1H,3'H-2,5'-bibenzo[d]imidazole (termed DPA 152), which is represented by the Formula (Ib):

(Ib)

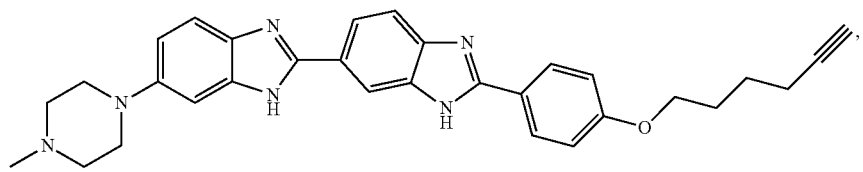

6-(4-methylpiperazin-1-yl)-2'-(4-(undec-10-ynyloxy)phenyl)-1H,3'H-2,5'-bibenzo[d]imidazole (termed DPA 153), which is represented by the Formula (Ic):

(Ic)

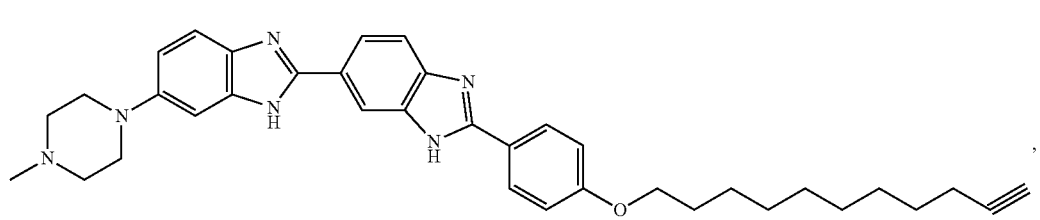

and
  6-(4-methylpiperazin-1-yl)-2'-(4-(4-(prop-2-ynyloxy)bu-toxy)phenyl)-1H,3'H-2,5'-bibenzo[d]imidazole (termed DPA 154), which is represented by the Formula (Id):

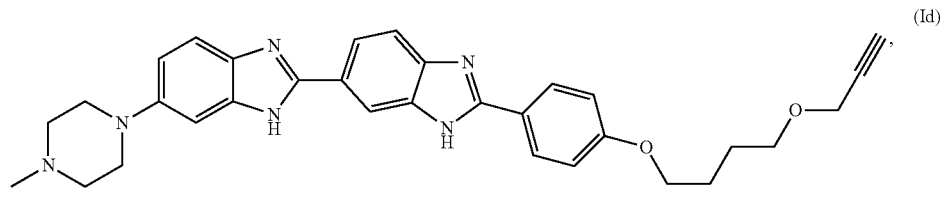 [SMILES: C#CCOCCCCOc1ccc(-c2nc3ccc(-c4nc5ccc(N6CCN(C)CC6)cc5[nH]4)cc3[nH]2)cc1]

(Id)

and salts thereof.

9. The method, according to claim 7, wherein the compound is:
  6-(4-methylpiperazin-1-yl)-2'-(4-(prop-2-ynyloxy)phe-nyl)-1H,3'H-2,5'-bibenzo[d]imidazole (termed DPA 151), which is represented by the Formula (Ia):

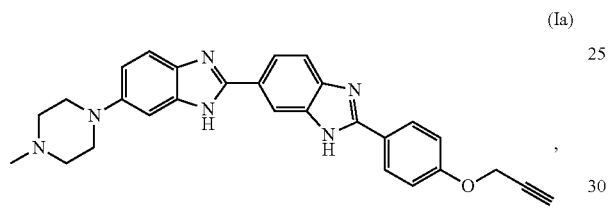

(Ia)

or a salt thereof.

10. The compound, according to claim 1, which is
  6-(4-methylpiperazin-1-yl)-2'-(4-(4-(prop-2-ynyloxy)bu-toxy)phenyl)-1H,3'H-2,5'-bibenzo[d]imidazole (termed DPA 154), which is represented by the Formula (Id):

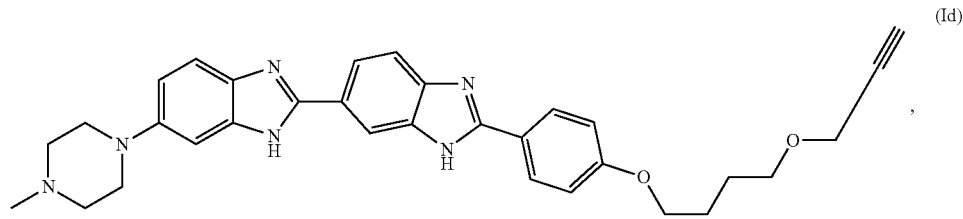 [SMILES: C#CCCOCCCCOc1ccc(-c2nc3ccc(-c4nc5ccc(N6CCN(C)CC6)cc5[nH]4)cc3[nH]2)cc1]

(Id)

or a salt thereof.

11. The method, according to claim 7, wherein the compound is:
  2'-(4-(hex-5-ynyloxy)phenyl)-6-(4-methylpiperazin-1-yl)-1H,3'H-2,5'-bibenzo[d]imidazole (termed DPA 152), which is represented by the Formula (Ib):

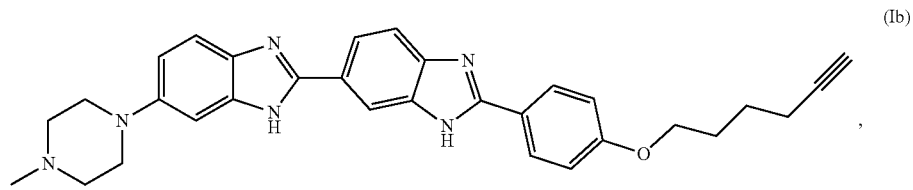 [SMILES: C#CCCCCOc1ccc(-c2nc3ccc(-c4nc5ccc(N6CCN(C)CC6)cc5[nH]4)cc3[nH]2)cc1]

(Ib)

or a salt thereof.

12. The method, according to claim 7, wherein the compound is:
6-(4-methylpiperazin-1-yl)-2'-(4-(undec-10-ynyloxy)phenyl)-1H,3'H-2,5'-bibenzo[d]imidazole (termed DPA 153), which is represented by the Formula (Ic):

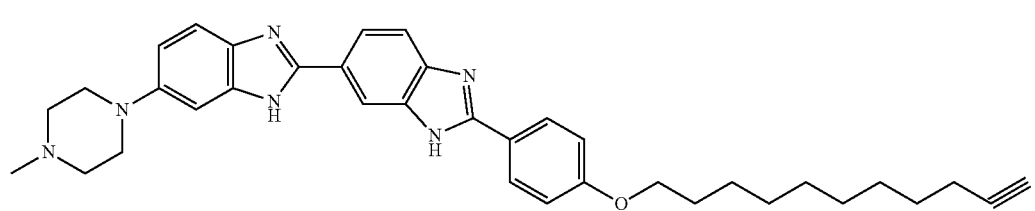

(Ic)

or a salt thereof.

13. The method, according to claim 7, wherein the compound is:
6-(4-methylpiperazin-1-yl)-2'-(4-(4-(prop-2-ynyloxy)butoxy)phenyl)-1H,3'H-2,5'-bibenzo[d]imidazole (termed DPA 154), which is represented by the Formula (Id):

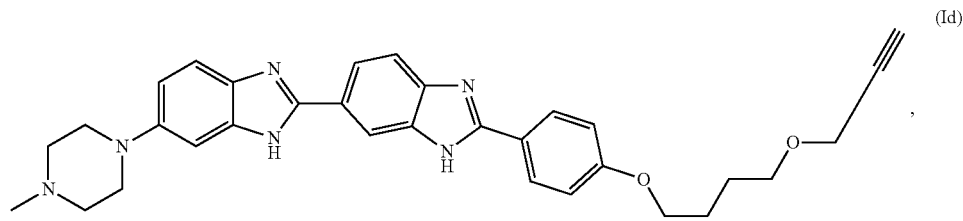 [SMILES: C#CCCOCCCCOc1ccc(-c2nc3ccc(-c4nc5ccc(N6CCN(C)CC6)cc5[nH]4)cc3[nH]2)cc1]

(Id)

or a salt thereof.

* * * * *

UNITED STATES PATENT AND TRADEMARK OFFICE
CERTIFICATE OF CORRECTION

PATENT NO. : 9,920,014 B2
APPLICATION NO. : 15/022868
DATED : March 20, 2018
INVENTOR(S) : Nihar Ranjan et al.

It is certified that error appears in the above-identified patent and that said Letters Patent is hereby corrected as shown below:

On the Title Page

"(71) Applicants: THE FLORIDA INTERNATIONAL BOARD OF TRUSTEES MODESTO A. MAIDIQUE CAMPUS, Miami, FL (US)" should read -- (71) Applicants: THE FLORIDA INTERNATIONAL BOARD OF TRUSTEES, Miami, FL (US); --

Signed and Sealed this
Tenth Day of July, 2018

Andrei Iancu
*Director of the United States Patent and Trademark Office*